US011213638B2

(12) United States Patent
Nettenstrom et al.

(10) Patent No.: US 11,213,638 B2
(45) Date of Patent: Jan. 4, 2022

(54) VAPOR PROVISION SYSTEM

(71) Applicant: NICOVENTURES HOLDINGS LIMITED, London (GB)

(72) Inventors: Matthew Joel Nettenstrom, London (GB); David Leadley, London (GB); Steven Michael Schennum, London (GB); Kenny Otiaba, London (GB)

(73) Assignee: Nicoventures Trading Limited, London (GB)

( * ) Notice: Subject to any disclaimer, the term of this patent is extended or adjusted under 35 U.S.C. 154(b) by 57 days.

(21) Appl. No.: 16/086,997

(22) PCT Filed: Mar. 21, 2017

(86) PCT No.: PCT/GB2017/050789
§ 371 (c)(1),
(2) Date: Sep. 20, 2018

(87) PCT Pub. No.: WO2017/163052
PCT Pub. Date: Sep. 28, 2017

(65) Prior Publication Data
US 2019/0046745 A1    Feb. 14, 2019

(30) Foreign Application Priority Data

Mar. 24, 2016  (GB) ...................................... 1605100
Jul. 21, 2016  (GB) ...................................... 1612684

(51) Int. Cl.
*A24F 47/00* (2020.01)
*A61M 11/04* (2006.01)
(Continued)

(52) U.S. Cl.
CPC ............. *A61M 15/06* (2013.01); *A24F 40/42* (2020.01); *A24F 40/44* (2020.01); *A61M 11/042* (2014.02);
(Continued)

(58) Field of Classification Search
None
See application file for complete search history.

(56) References Cited

U.S. PATENT DOCUMENTS 3,614,956 A   10/1971  Thornton et al.
3,888,253 A    6/1975  Watt et al.
(Continued)

FOREIGN PATENT DOCUMENTS

AT           508244 A4   12/2010
AU      2017236411 B2    6/2019
(Continued)

OTHER PUBLICATIONS

Decision for Korean Application No. 3020160038357_M002 dated Dec. 14, 2016., 3 pages.
(Continued)

*Primary Examiner* — Thor S Campbell
(74) *Attorney, Agent, or Firm* — Patterson Thuente Pedersen, P.A.

(57) ABSTRACT

A cartomizer for a vapor provision system, the cartomizer including: a container for holding a reservoir of free liquid to be vaporized; an atomizing chamber; a porous wick extending from inside the container, through an aperture in a wall of the atomizing chamber, to inside the atomizing chamber in order to convey the liquid from the reservoir to the inside of the atomizing chamber for vaporization; and a resilient seal provided in the aperture to restrict the liquid from entering the atomizing chamber from the reservoir except by travelling along the wick.

26 Claims, 13 Drawing Sheets

(51) Int. Cl.

| | | |
|---|---|---|
| *A24F 40/44* | (2020.01) | |
| *A61M 15/06* | (2006.01) | |
| *A61M 15/00* | (2006.01) | |
| *A24F 40/42* | (2020.01) | |
| *A61M 16/00* | (2006.01) | |
| *A24F 40/10* | (2020.01) | |
| *A24F 40/485* | (2020.01) | |

(52) U.S. Cl.
CPC ...... *A61M 15/002* (2014.02); *A61M 15/0021* (2014.02); *A24F 40/10* (2020.01); *A24F 40/485* (2020.01); *A61M 2016/0018* (2013.01); *A61M 2016/0021* (2013.01); *A61M 2205/3334* (2013.01); *A61M 2205/3375* (2013.01); *A61M 2205/3653* (2013.01); *A61M 2205/8206* (2013.01)

(56) References Cited

U.S. PATENT DOCUMENTS

| | | |
|---|---|---|
| 4,022,221 A | 5/1977 | Berger |
| D250,485 S | 12/1978 | Cuthbertson |
| 4,517,996 A | 5/1985 | Vester |
| 4,602,647 A | 7/1986 | Wiethaup et al. |
| 4,655,229 A | 4/1987 | Sensabaugh, Jr. et al. |
| 4,945,929 A | 8/1990 | Egilmex |
| D367,526 S | 2/1996 | Bignon |
| 5,564,442 A | 10/1996 | MacDonald et al. |
| D430,358 S | 8/2000 | Papiernik |
| 6,182,655 B1 | 2/2001 | Keller et al. |
| D447,276 S | 8/2001 | Gustafson |
| 6,418,926 B1 | 7/2002 | Chawla |
| 6,446,880 B1 | 9/2002 | Schram et al. |
| D466,644 S | 12/2002 | Cohen Harel |
| D469,962 S | 2/2003 | Campbell et al. |
| D503,996 S | 4/2005 | Mabbutt |
| D504,947 S | 5/2005 | McAuley et al. |
| D505,514 S | 5/2005 | Liu |
| D514,222 S | 1/2006 | Anderson et al. |
| D518,171 S | 3/2006 | Anderson et al. |
| D560,793 S | 1/2008 | Pearl et al. |
| D569,967 S | 5/2008 | Pearl et al. |
| D572,406 S | 7/2008 | Masoud |
| D577,815 S | 9/2008 | Gokhale et al. |
| D579,544 S | 10/2008 | Birath et al. |
| D579,545 S | 10/2008 | Birath et al. |
| D579,546 S | 10/2008 | Birath et al. |
| D579,547 S | 10/2008 | Birath et al. |
| D579,548 S | 10/2008 | Birath et al. |
| D579,549 S | 10/2008 | Birath et al. |
| D579,550 S | 10/2008 | Birath et al. |
| D581,520 S | 11/2008 | Williams et al. |
| D583,463 S | 12/2008 | Wood et al. |
| D590,495 S | 4/2009 | Lulla et al. |
| D590,938 S | 4/2009 | Lulla et al. |
| D591,856 S | 5/2009 | Lulla et al. |
| D613,848 S | 4/2010 | Harvey et al. |
| D614,285 S | 4/2010 | Birath et al. |
| D629,886 S | 12/2010 | Adamo et al. |
| D637,280 S | 5/2011 | Harvey et al. |
| D637,281 S | 5/2011 | Harvey et al. |
| D637,282 S | 5/2011 | Harvey et al. |
| D639,414 S | 6/2011 | Berndt |
| D641,076 S | 7/2011 | Grunstad et al. |
| D646,780 S | 10/2011 | Lulla et al. |
| D659,236 S | 5/2012 | Bobjer et al. |
| D670,374 S | 11/2012 | Bobjer et al. |
| D671,207 S | 11/2012 | Bobjer et al. |
| D684,254 S | 6/2013 | Zuyderhoudt |
| D684,684 S | 6/2013 | Grunstad et al. |
| D692,997 S | 11/2013 | Lovell et al. |
| D693,963 S | 11/2013 | Akopyan |
| 8,602,210 B2 | 12/2013 | Milner et al. |
| D700,227 S | 2/2014 | Kile |
| D700,738 S | 3/2014 | Rennick et al. |
| D710,002 S | 7/2014 | Valentine et al. |
| D711,528 S | 8/2014 | Grunstad et al. |
| D717,425 S | 11/2014 | Von Schuckmann |
| D726,364 S | 4/2015 | Weigensberg |
| D726,955 S | 4/2015 | Martin |
| D737,419 S | 8/2015 | Emarlou |
| D737,426 S | 8/2015 | Nakamura |
| 9,155,336 B2* | 10/2015 | Liu ............... A24F 47/008 |
| D745,139 S | 12/2015 | Chen et al. |
| D745,660 S | 12/2015 | Gruntad et al. |
| D761,488 S | 7/2016 | Alarcon et al. |
| D769,438 S | 10/2016 | Crosby et al. |
| D770,088 S | 10/2016 | Abadi et al. |
| D782,109 S | 3/2017 | King |
| D790,123 S | 6/2017 | Beer et al. |
| D790,125 S | 6/2017 | Beer et al. |
| D790,767 S | 6/2017 | Rush et al. |
| D799,750 S | 10/2017 | Parcevaux |
| 9,956,357 B2* | 5/2018 | Chen ............... A24F 47/008 |
| 9,964,300 B2* | 5/2018 | Liu ............... A24F 47/008 |
| D820,514 S | 6/2018 | Durand |
| D820,515 S | 6/2018 | Nettenstrom et al. |
| D822,193 S | 7/2018 | Nitta |
| 10,010,109 B2* | 7/2018 | Janardhan ............ A24F 47/008 |
| 10,058,122 B2 | 8/2018 | Steingraber et al. |
| D852,408 S | 6/2019 | Nettenstrom et al. |
| 10,653,186 B2 | 5/2020 | Verleur et al. |
| 2002/0040713 A1 | 4/2002 | Eisele et al. |
| 2003/0178024 A1 | 9/2003 | Allan et al. |
| 2003/0235538 A1 | 12/2003 | Zierenberg |
| 2004/0003820 A1 | 1/2004 | Iannuzzi |
| 2004/0025865 A1 | 2/2004 | Nichols et al. |
| 2004/0025877 A1 | 2/2004 | Crowder et al. |
| 2004/0118936 A1 | 6/2004 | Schram et al. |
| 2004/0149283 A1 | 8/2004 | Hochrainer |
| 2004/0244810 A1* | 12/2004 | Henninger ............ A45D 2/36 132/228 |
| 2005/0005934 A1 | 1/2005 | Harvey |
| 2005/0006273 A1 | 1/2005 | Chawla |
| 2005/0017017 A1 | 1/2005 | Crosby et al. |
| 2005/0022812 A1 | 2/2005 | Hrkach |
| 2005/0103336 A1 | 5/2005 | Nishibayashi et al. |
| 2005/0103337 A1 | 5/2005 | Hickey et al. |
| 2005/0115562 A1 | 6/2005 | Chawla |
| 2005/0205685 A1 | 9/2005 | Jones |
| 2005/0252511 A1 | 11/2005 | Pentafragas |
| 2005/0279357 A1 | 12/2005 | Wachtel |
| 2006/0102175 A1 | 5/2006 | Nelson |
| 2006/0157053 A1 | 7/2006 | Barney et al. |
| 2006/0157054 A1 | 7/2006 | Kuehn et al. |
| 2006/0163269 A1 | 7/2006 | Anderson et al. |
| 2006/0237010 A1 | 10/2006 | De Boer et al. |
| 2006/0237016 A1 | 10/2006 | Wachtel |
| 2007/0045288 A1 | 3/2007 | Nelson |
| 2007/0052544 A1 | 3/2007 | Lintell |
| 2007/0102016 A1 | 5/2007 | Xiahou |
| 2007/0114305 A1 | 5/2007 | Yamaguchi et al. |
| 2007/0125765 A1 | 6/2007 | Nelson |
| 2007/0131805 A1 | 6/2007 | Yamaguchi et al. |
| 2007/0137645 A1 | 6/2007 | Eason et al. |
| 2007/0152086 A1 | 7/2007 | Yamaguchi et al. |
| 2007/0181123 A1 | 8/2007 | Houzego |
| 2007/0215149 A1 | 9/2007 | King et al. |
| 2007/0267032 A1 | 11/2007 | Shan |
| 2007/0295332 A1 | 12/2007 | Ziegler et al. |
| 2008/0099015 A1 | 5/2008 | Pocock et al. |
| 2008/0116220 A1 | 5/2008 | Pocock et al. |
| 2008/0196718 A1 | 8/2008 | Connell et al. |
| 2008/0295832 A1 | 12/2008 | Geser et al. |
| 2008/0295834 A1 | 12/2008 | Thoemmes et al. |
| 2008/0314384 A1 | 12/2008 | Harris et al. |
| 2009/0084379 A1 | 4/2009 | Goeckner et al. |
| 2009/0165791 A1 | 7/2009 | Wendland |
| 2009/0194105 A1 | 8/2009 | Besseler et al. |
| 2009/0205656 A1 | 8/2009 | Nishibayashi et al. |
| 2009/0250056 A1 | 10/2009 | Pentafragas |
| 2009/0277446 A1 | 11/2009 | Walz |
| 2009/0283095 A1 | 11/2009 | Pocock et al. |

(56) References Cited

U.S. PATENT DOCUMENTS

| | | | |
|---|---|---|---|
| 2009/0293888 A1 | 12/2009 | Williams et al. | |
| 2009/0293892 A1 | 12/2009 | Williams et al. | |
| 2009/0314291 A1 | 12/2009 | Anderson et al. | |
| 2010/0024812 A1 | 2/2010 | Sugita et al. | |
| 2010/0024814 A1 | 2/2010 | Sugita et al. | |
| 2010/0059050 A1 | 3/2010 | Wachtel | |
| 2010/0059052 A1 | 3/2010 | Davies et al. | |
| 2010/0078022 A1 | 4/2010 | Striebig et al. | |
| 2010/0083962 A1 | 4/2010 | Von Schuckmann | |
| 2010/0154795 A1 | 6/2010 | Pentafragas | |
| 2010/0163042 A1 | 7/2010 | Bhowmick et al. | |
| 2010/0189780 A1 | 7/2010 | Walz et al. | |
| 2010/0192949 A1 | 8/2010 | Wright et al. | |
| 2010/0242960 A1 | 9/2010 | Zangerle | |
| 2010/0258120 A1 | 10/2010 | Colomb | |
| 2010/0261403 A1 | 10/2010 | Shishido | |
| 2010/0294278 A1 | 11/2010 | Mosier et al. | |
| 2010/0313886 A1 | 12/2010 | Wachtel et al. | |
| 2011/0036346 A1 | 2/2011 | Cohen et al. | |
| 2011/0041841 A1 | 2/2011 | Wachtel et al. | |
| 2011/0067696 A1 | 3/2011 | Sato et al. | |
| 2011/0094523 A1 | 4/2011 | Thorens et al. | |
| 2011/0120463 A1 | 5/2011 | Esteve et al. | |
| 2011/0120465 A1 | 5/2011 | Haerder et al. | |
| 2011/0162642 A1 | 7/2011 | Akouka et al. | |
| 2011/0174305 A1 | 7/2011 | Bunch et al. | |
| 2011/0203586 A1 | 8/2011 | Egen et al. | |
| 2011/0226236 A1 | 9/2011 | Buchberger | |
| 2011/0232637 A1 | 9/2011 | Kaemper et al. | |
| 2011/0271958 A1 | 11/2011 | Sawant | |
| 2011/0277757 A1 | 11/2011 | Terry et al. | |
| 2011/0277760 A1 | 11/2011 | Terry et al. | |
| 2012/0037157 A1 | 2/2012 | Rohrschneider et al. | |
| 2012/0037158 A1 | 2/2012 | Wachtel et al. | |
| 2012/0132205 A1 | 5/2012 | Meliniotis et al. | |
| 2012/0247463 A1 | 10/2012 | Zoltan | |
| 2012/0260917 A1 | 10/2012 | Bilgic | |
| 2013/0047985 A1 | 2/2013 | Harris et al. | |
| 2013/0074857 A1 | 3/2013 | Buchberger | |
| 2013/0139815 A1 | 6/2013 | Colomb et al. | |
| 2013/0152927 A1 | 6/2013 | Baillet et al. | |
| 2013/0152928 A1 | 6/2013 | Kirniak | |
| 2013/0174842 A1 | 7/2013 | Young et al. | |
| 2013/0186398 A1 | 7/2013 | Baillet et al. | |
| 2013/0192615 A1 | 8/2013 | Tucker et al. | |
| 2013/0228191 A1* | 9/2013 | Newton | A24F 47/008 131/329 |
| 2013/0233313 A1 | 9/2013 | Young et al. | |
| 2013/0255679 A1 | 10/2013 | Andrade et al. | |
| 2013/0269695 A1 | 10/2013 | Brouet et al. | |
| 2013/0306065 A1* | 11/2013 | Thorens | A24F 47/008 128/202.21 |
| 2014/0000601 A1 | 1/2014 | Arvidsson et al. | |
| 2014/0007875 A1 | 1/2014 | Berg et al. | |
| 2014/0076315 A1 | 3/2014 | Von Schuckmann | |
| 2014/0083422 A1 | 3/2014 | Arvidsson et al. | |
| 2014/0109921 A1 | 4/2014 | Chen | |
| 2014/0123989 A1* | 5/2014 | Lamothe | H05B 3/06 131/328 |
| 2014/0196717 A1 | 7/2014 | Liu | |
| 2014/0238422 A1 | 8/2014 | Plunkett et al. | |
| 2014/0238424 A1 | 8/2014 | Macko et al. | |
| 2014/0290653 A1 | 10/2014 | Colomb | |
| 2014/0299125 A1 | 10/2014 | Buchberger | |
| 2014/0318538 A1 | 10/2014 | Bilgic | |
| 2014/0360514 A1 | 12/2014 | Zhu | |
| 2014/0376895 A1 | 12/2014 | Han | |
| 2015/0027454 A1 | 1/2015 | Li et al. | |
| 2015/0027456 A1 | 1/2015 | Janardhan et al. | |
| 2015/0027457 A1 | 1/2015 | Janardhan et al. | |
| 2015/0034104 A1 | 2/2015 | Zhou | |
| 2015/0059747 A1 | 3/2015 | Von Schuckmann | |
| 2015/0068541 A1 | 3/2015 | Sears et al. | |
| 2015/0080808 A1 | 3/2015 | Esteve et al. | |
| 2015/0083129 A1 | 3/2015 | Colomb et al. | |
| 2015/0086804 A1 | 3/2015 | Schorn et al. | |
| 2015/0096563 A1 | 4/2015 | Toksoz et al. | |
| 2015/0107590 A1 | 4/2015 | Colomb | |
| 2015/0114391 A1 | 4/2015 | Colomb et al. | |
| 2015/0114393 A1 | 4/2015 | Von Schuckmann | |
| 2015/0122276 A1 | 5/2015 | Johnson et al. | |
| 2015/0122277 A1 | 5/2015 | Frobisher et al. | |
| 2015/0128938 A1 | 5/2015 | Colomb et al. | |
| 2015/0128977 A1 | 5/2015 | Li et al. | |
| 2015/0144145 A1* | 5/2015 | Chang | A24F 40/42 131/328 |
| 2015/0144147 A1 | 5/2015 | Li et al. | |
| 2015/0164142 A1 | 6/2015 | Li et al. | |
| 2015/0174346 A1 | 6/2015 | Dhuppad et al. | |
| 2015/0208730 A1 | 7/2015 | Li et al. | |
| 2015/0216237 A1 | 8/2015 | Wensley et al. | |
| 2015/0257446 A1 | 9/2015 | Chung | |
| 2015/0297841 A1 | 10/2015 | Ono | |
| 2015/0298893 A1 | 10/2015 | Welp | |
| 2015/0314085 A1 | 11/2015 | Banoun | |
| 2015/0320116 A1 | 11/2015 | Bleloch et al. | |
| 2015/0335075 A1 | 11/2015 | Minskoff et al. | |
| 2015/0342256 A1 | 12/2015 | Chen | |
| 2015/0343159 A1 | 12/2015 | Farr et al. | |
| 2016/0001018 A1 | 1/2016 | Fink et al. | |
| 2016/0001019 A1 | 1/2016 | Fink et al. | |
| 2016/0007654 A1 | 1/2016 | Zhu | |
| 2016/0015082 A1* | 1/2016 | Liu | A24F 47/008 131/329 |
| 2016/0015912 A1 | 1/2016 | De Kruijf et al. | |
| 2016/0021934 A1* | 1/2016 | Cadieux | A24F 47/008 131/328 |
| 2016/0022931 A1 | 1/2016 | Althorpe et al. | |
| 2016/0045684 A1 | 2/2016 | Ono | |
| 2016/0050975 A1 | 2/2016 | Worm et al. | |
| 2016/0109115 A1 | 4/2016 | Lipowicz | |
| 2016/0128386 A1 | 5/2016 | Chen | |
| 2016/0143365 A1 | 5/2016 | Liu | |
| 2016/0151589 A1 | 6/2016 | Ohrt et al. | |
| 2016/0158470 A1 | 6/2016 | Esteve et al. | |
| 2016/0175547 A1 | 6/2016 | Nakamura | |
| 2016/0219936 A1 | 8/2016 | Alarcon | |
| 2016/0264290 A1 | 9/2016 | Hafer et al. | |
| 2016/0279354 A1 | 9/2016 | De Kruijf et al. | |
| 2016/0287818 A1 | 10/2016 | Colomb et al. | |
| 2016/0338411 A1 | 11/2016 | Liu | |
| 2016/0346488 A1 | 12/2016 | Beller | |
| 2016/0367767 A1 | 12/2016 | Cashman et al. | |
| 2016/0375207 A1 | 12/2016 | Bhide et al. | |
| 2017/0035117 A1 | 2/2017 | Lin | |
| 2017/0056608 A1 | 3/2017 | McDerment et al. | |
| 2017/0064999 A1 | 3/2017 | Perez et al. | |
| 2017/0119057 A1 | 5/2017 | Liu | |
| 2017/0127728 A1 | 5/2017 | Li et al. | |
| 2017/0208866 A1 | 7/2017 | Liu | |
| 2017/0231281 A1 | 8/2017 | Hatton et al. | |
| 2017/0231282 A1 | 8/2017 | Bowen et al. | |
| 2017/0280773 A1* | 10/2017 | Force | H05B 3/04 |
| 2017/0280778 A1* | 10/2017 | Force | A24F 47/008 |
| 2017/0325504 A1 | 11/2017 | Liu | |
| 2017/0360092 A1 | 12/2017 | Althorpe et al. | |
| 2018/0007960 A1 | 1/2018 | Suzuki et al. | |
| 2018/0035718 A1 | 2/2018 | Liu | |
| 2018/0213845 A1 | 8/2018 | Qiu | |
| 2018/0220708 A1 | 8/2018 | Scott et al. | |
| 2018/0228216 A1 | 8/2018 | Saygili | |
| 2018/0352867 A1 | 12/2018 | Kane et al. | |
| 2019/0022345 A1 | 1/2019 | Kotch | |
| 2019/0053542 A1 | 2/2019 | Chen | |
| 2019/0083720 A1 | 3/2019 | Leadley et al. | |
| 2019/0098931 A1 | 4/2019 | Leadley et al. | |
| 2019/0230991 A1 | 8/2019 | Liu et al. | |
| 2020/0138117 A1* | 5/2020 | Rosser | A24F 40/485 |
| 2020/0146360 A1* | 5/2020 | Rosser | A24F 40/42 |
| 2020/0154770 A1* | 5/2020 | Hepworth | A61M 11/042 |
| 2020/0281270 A1* | 9/2020 | Potter | A24F 40/46 |

(56) References Cited

U.S. PATENT DOCUMENTS

| | | |
|---|---|---|
| 2020/0367557 A1 | 11/2020 | Lin et al. |
| 2020/0375263 A1 | 12/2020 | Chen |

FOREIGN PATENT DOCUMENTS

| | | |
|---|---:|---|
| AU | 2017236564 B2 | 11/2019 |
| CA | 2505366 A1 | 10/2006 |
| CL | 2018002640 A1 | 12/2018 |
| CL | 2018002657 A1 | 12/2018 |
| CL | 2018002658 A1 | 12/2018 |
| CN | 2698098 Y | 5/2005 |
| CN | 2827020 Y | 10/2006 |
| CN | 1906096 A | 1/2007 |
| CN | 300865525-D | 9/2007 |
| CN | 300840847-D | 10/2008 |
| CN | 300867097-D | 12/2008 |
| CN | 101400397 A | 4/2009 |
| CN | 101468218 A | 7/2009 |
| CN | 101574552 A | 11/2009 |
| CN | 301347038 S | 12/2009 |
| CN | 301433957 S | 6/2010 |
| CN | 201791251 U | 4/2011 |
| CN | 202085710 U | 12/2011 |
| CN | 302012774 S | 3/2012 |
| CN | 102655773 A | 9/2012 |
| CN | 302216014 S | 12/2012 |
| CN | 103118726 A | 5/2013 |
| CN | 103237570 A | 8/2013 |
| CN | 302926278 S | 1/2014 |
| CN | 203492795 U | 3/2014 |
| CN | 203523806 U | 4/2014 |
| CN | 203872998 U | 10/2014 |
| CN | 104254258 A | 12/2014 |
| CN | 204015104 U | 12/2014 |
| CN | 104544567 A | 4/2015 |
| CN | 104544570 A | 4/2015 |
| CN | 303162040 S | 4/2015 |
| CN | 303192526 S | 4/2015 |
| CN | 104605482 A | 5/2015 |
| CN | 204317491 U | 5/2015 |
| CN | 303227659 S | 5/2015 |
| CN | 303417607 | 5/2015 |
| CN | 104720114 A | 6/2015 |
| CN | 303234670 S | 6/2015 |
| CN | 303250845 S | 6/2015 |
| CN | 303442703 S | 6/2015 |
| CN | 303535276 S | 6/2015 |
| CN | 104770882 A | 7/2015 |
| CN | 204426686 U | 7/2015 |
| CN | 204444245 U | 7/2015 |
| CN | 303273075 S | 7/2015 |
| CN | 303279026 S | 7/2015 |
| CN | 303300421 S | 7/2015 |
| CN | 303300422 S | 7/2015 |
| CN | 104824846 A | 8/2015 |
| CN | 204519363 U | 8/2015 |
| CN | 303322969 S | 8/2015 |
| CN | 303322971 S | 8/2015 |
| CN | 303322985 S | 8/2015 |
| CN | 303341926 S | 8/2015 |
| CN | 303350911 S | 8/2015 |
| CN | 104921308 A | 9/2015 |
| CN | 204617062 U | 9/2015 |
| CN | 303361183 S | 9/2015 |
| CN | 303380240 S | 9/2015 |
| CN | 303380242 S | 9/2015 |
| CN | 303380243 S | 9/2015 |
| CN | 303380252 S | 9/2015 |
| CN | 303417611 S | 10/2015 |
| CN | 105011380 A | 11/2015 |
| CN | 303470028 S | 11/2015 |
| CN | 105455197 A | 4/2016 |
| CN | 105455197 B | 1/2019 |
| DE | 95102980001 | 9/1996 |
| DE | 96072850001 | 4/1997 |
| DE | 96072850002 | 4/1997 |
| DE | 499019970001 | 7/1999 |
| DE | 499019970002 | 7/1999 |
| DE | 400039090001 | 8/2000 |
| DE | 401071010001 | 2/2002 |
| DE | 402003030001 | 8/2002 |
| DE | 402093100001 | 3/2003 |
| DE | 402093100002 | 3/2003 |
| DE | 402093100003 | 3/2003 |
| DE | 402093100004 | 3/2003 |
| DE | 402093100005 | 3/2003 |
| DE | 403019480001 | 7/2003 |
| DE | 202013010929 U1 | 12/2013 |
| DE | 96072850003 | 3/2016 |
| EA | 019736 B1 | 5/2014 |
| EM | 0001050440001 | 6/2003 |
| EM | 0001050440002 | 6/2003 |
| EM | 0005457690001 | 6/2006 |
| EM | 0007369620001 | 6/2007 |
| EM | 0007369620002 | 6/2007 |
| EM | 0007369620003 | 6/2007 |
| EM | 0007369620004 | 6/2007 |
| EM | 0007369620005 | 6/2007 |
| EM | 0007369620006 | 6/2007 |
| EM | 0007369620007 | 6/2007 |
| EM | 0007369620008 | 6/2007 |
| EM | 0008611410001 | 1/2008 |
| EM | 0015105870001 | 5/2009 |
| EM | 0015105870002 | 5/2009 |
| EM | 0013233070007 | 4/2012 |
| EM | 0013233070008 | 4/2012 |
| EM | 0013233070009 | 4/2012 |
| EM | 0013233070010 | 4/2012 |
| EM | 0013233070011 | 4/2012 |
| EM | 0013233070012 | 4/2012 |
| EM | 0024296960003 | 3/2014 |
| EM | 0024296960004 | 3/2014 |
| EM | 0014157800001 | 7/2014 |
| EM | 0014157800002 | 7/2014 |
| EM | 0014157800003 | 7/2014 |
| EM | 0014157800004 | 7/2014 |
| EM | 0014157800005 | 7/2014 |
| EM | 0014157800006 | 7/2014 |
| EM | 0014157800007 | 7/2014 |
| EM | 0014157800008 | 7/2014 |
| EM | 0014157800009 | 7/2014 |
| EM | 0026967650003 | 5/2015 |
| EM | 0029228640002 | 12/2015 |
| EP | 1496858 A1 | 1/2005 |
| EP | 2319334 A1 | 5/2011 |
| EP | 2460424 A1 | 6/2012 |
| EP | 1496858 B1 | 8/2013 |
| EP | 2801270 A2 | 11/2014 |
| EP | 2875740 A2 | 5/2015 |
| EP | 2878213 A1 | 6/2015 |
| EP | 3039976 A1 | 7/2016 |
| EP | 3292775 A1 | 3/2018 |
| FR | 970852009 | 8/1997 |
| FR | 983203001 | 10/1998 |
| FR | 956833001 | 1/1999 |
| FR | 001967001 | 7/2000 |
| FR | 007595001 | 4/2001 |
| FR | 007595002 | 4/2001 |
| FR | 011038001 | 5/2001 |
| FR | 011152001 | 5/2001 |
| FR | 011154001 | 5/2001 |
| FR | 201125490001 | 7/2011 |
| FR | 201127120001 | 7/2011 |
| FR | 201127120002 | 7/2011 |
| FR | 201127120003 | 7/2011 |
| FR | 2962339 A1 | 1/2012 |
| FR | 20124875012 | 8/2013 |
| FR | 3039039 A1 | 1/2017 |
| GB | 488340 A | 7/1938 |
| GB | 911405 A | 11/1962 |
| GB | 2047060 A | 11/1980 |
| GB | 2115679 A | 9/1983 |
| GB | 1029228 | 4/1986 |
| GB | 2191718 A | 12/1987 |

(56) References Cited

FOREIGN PATENT DOCUMENTS

| | | |
|---|---|---|
| GB | 2048538 | 11/1995 |
| GB | 2055446 | 8/1996 |
| GB | 2075058 | 9/1998 |
| GB | 2093858 | 8/2000 |
| GB | 2093859 | 8/2000 |
| GB | 2412876 A | 10/2005 |
| GB | 4020185 | 11/2011 |
| GB | 2504077 A | 1/2014 |
| GB | 2508520 A | 6/2014 |
| GB | 2515562 A | 12/2014 |
| GB | 4041108 | 6/2015 |
| IT | 1993MIO0001280003 | 3/1993 |
| IT | 2000TOO0002350001 | 9/2000 |
| IT | 2000TOO0002350003 | 9/2000 |
| IT | 2000TOO0002350004 | 9/2000 |
| IT | 2000TOO0002350006 | 9/2000 |
| IT | 2002TOO000214003 | 9/2002 |
| IT | 2002TOO000214004 | 9/2002 |
| IT | 2002TOO0002140001 | 9/2002 |
| IT | 2002TOO0002140002 | 9/2002 |
| JP | H0712849 Y2 | 3/1995 |
| JP | H08322934 A | 12/1996 |
| JP | H08511966 A | 12/1996 |
| JP | 2002525178 A | 8/2002 |
| JP | 2005525393 A | 8/2005 |
| JP | 2007501271 A | 1/2007 |
| JP | 2007502683 A | 2/2007 |
| JP | 2007511437 A | 5/2007 |
| JP | 2009536062 A | 10/2009 |
| JP | 2013507976 A | 3/2013 |
| JP | 2013545473 A | 12/2013 |
| JP | 2014519850 A | 8/2014 |
| JP | 2014237011 A | 12/2014 |
| JP | 2015504653 A | 2/2015 |
| JP | 2015526266 A | 9/2015 |
| JP | D1575098 S | 3/2017 |
| JP | 2017522873 A | 8/2017 |
| JP | 6621154 B2 | 12/2019 |
| KR | 100495099 B1 | 11/2005 |
| KR | 20120098343 A | 9/2012 |
| KR | 101256914 B1 | 4/2013 |
| KR | 20150036557 A | 4/2015 |
| KZ | 30993 B | 3/2016 |
| RU | 115629 U1 | 5/2012 |
| RU | 122000 U1 | 11/2012 |
| RU | 2536032 C2 | 12/2014 |
| RU | 2698528 C1 | 8/2019 |
| UA | 109556 C2 | 9/2015 |
| WO | WO-DM264451 | 6/1993 |
| WO | WO-DM0264451 | 6/1996 |
| WO | WO-9912596 A1 | 3/1999 |
| WO | WO-0205881 A1 | 1/2002 |
| WO | WO-03095005 A1 | 11/2003 |
| WO | WO-2007007110 A1 | 1/2007 |
| WO | WO-2009050827 A1 | 4/2009 |
| WO | WO-2009092520 A1 | 7/2009 |
| WO | WO-2009092653 A1 | 7/2009 |
| WO | WO-2010114504 A1 | 10/2010 |
| WO | WO-2012004512 A1 | 1/2012 |
| WO | WO-2012004514 A1 | 1/2012 |
| WO | WO-2012004518 A1 | 1/2012 |
| WO | WO-2012010878 A1 | 1/2012 |
| WO | WO-2012047181 A1 | 4/2012 |
| WO | WO-2013083638 A1 | 6/2013 |
| WO | WO-2013118299 A1 | 8/2013 |
| WO | WO-2014066730 A1 | 5/2014 |
| WO | WO-2014135224 A1 | 9/2014 |
| WO | WO-2014159250 A1 | 10/2014 |
| WO | WO-2014201432 A1 | 12/2014 |
| WO | WO-2014204417 A1 | 12/2014 |
| WO | WO-2015006838 A1 | 1/2015 |
| WO | WO-2015022436 A1 | 2/2015 |
| WO | WO-2015073564 A1 | 5/2015 |
| WO | WO-2015112750 A1 | 7/2015 |
| WO | WO-2015113743 A1 | 8/2015 |
| WO | WO-2015117700 A1 | 8/2015 |
| WO | WO-2015166239 A1 | 11/2015 |
| WO | WO-2015173303 A1 | 11/2015 |
| WO | WO-2015175568 A1 | 11/2015 |
| WO | WO-2016005600 A1 | 1/2016 |
| WO | WO-2016014652 A1 | 1/2016 |
| WO | WO-2016079410 A1 | 5/2016 |
| WO | WO-2016107764 A2 | 7/2016 |
| WO | WO-2016107767 A1 | 7/2016 |
| WO | WO-2016118005 A1 | 7/2016 |
| WO | WO-2016122417 A1 | 8/2016 |
| WO | WO-2016150019 A1 | 9/2016 |
| WO | WO-2016159919 A1 | 10/2016 |
| WO | WO-2017011865 A1 | 1/2017 |
| WO | WO-2017013130 A1 | 1/2017 |
| WO | WO-DM094223001 | 1/2017 |
| WO | WO-2017024799 A1 | 2/2017 |
| WO | WO-2017163044 A1 | 9/2017 |
| WO | WO-2017163045 A1 | 9/2017 |
| WO | WO-2017163050 A1 | 9/2017 |
| WO | WO-2017163051 A1 | 9/2017 |
| WO | WO-2017163052 A1 | 9/2017 |
| WO | WO-2017206211 A1 | 12/2017 |

OTHER PUBLICATIONS

Decision mailed Mar. 14, 2017 for Ukrainian Application No. S201601341, 7 pages.
Decision to Grant a Patent mailed Oct. 23, 2019 for Japanese Application No. 2018-545824, 5 pages.
Decision to Grant mailed Mar. 27, 2019 for Russian Application No. 2018133622, 14 pages.
Decision to Grant mailed May 30, 2019 for Russian Application No. 2018132701, 14 pages.
Decision to Grant mailed Aug. 15, 2017 for Russian Application No. 201650539349, 4 pages.
Decision to Grant mailed Aug. 28, 2017 for Russian Application No. 201750018449, 4 pages.
Electronic Cigarette | Vype Pebble | Govype, post date n/a, (c)n/a, govype.com, Aug. 30, 2017, https://www.govype.com/uk/vype-pebble-starter-kit. cited by examiner, 2 pages.
Examination Report for Canadian Application No. 169756, dated Nov. 17, 2016, 1 page.
Formalities Notice No. 1 for Australian Design Application No. AU201614224, dated Aug. 9, 2016., 2 pages.
Formalities Notice No. 1 for Australian Design Application No. 201614225, dated Aug. 9, 2016, 2 pages.
Innokin EQ Pod System Vape Kit by vapeclub. dated 2018. found online [Sep. 24, 2018] https://www.vapeclub.co.uk/pods-and-closed-system-vape-starter--kits/innokin-eq-pod-system-vape-kit.html, 6 pages.
International Preliminary Report on Patentability for Application No. PCT/GB2017/050787, DATED Feb. 27, 2010, 12 pages.
International Search Report and Written Opinion for Application No. PCT/GB2017/050787, dated Jul. 3, 2017, 12 pages.
International Preliminary Report on Patentability for Application No. PCT/GB2017/050783, dated Jul. 6, 2018, 13 pages.
International Search Report and Written Opinion for Application No. PCT/GB2017/050783, dated Jun. 9, 2017, 15 pages.
International Preliminary Examining Authority for Application No. PCT/GB2017/050783, dated Jun. 12, 2018, 6 pages.
International Preliminary Report on Patentability for Application No. PCT/GB2017/050781, dated Feb. 27, 2018, 13 pages.
International Preliminary Report on Patentability for Application No. PCT/GB2017/050788, dated Aug. 3, 2018, 14 pages.
International Preliminary Report on Patentability for Application No. PCT/GB2017/050789, dated Jul. 11, 2018, 13 pages.
International Search Report and Written Opinion for Application No. PCT/GB2017/050781 dated Jun. 14, 2017.
International Search Report and Written Opinion for Application No. PCT/GB2017/050788, dated Jun. 7, 2017, 13 pages.
International Search Report and Written Opinion for Application No. PCT/GB2017/050789, dated Jun. 7, 2017, 9 pages.
International Second Written Opinion for PCT Application No. PCT/GB2017/050788, dated Mar. 7, 2018, 9 pages.

(56) References Cited

OTHER PUBLICATIONS

JustFog C601 Pod System Vape Kit by vapeclub. dated 2018. found online [Sep. 24, 2018] https://www.vapeclub.co.uk/pods-and-closed-system-vape-starter-kits/justfog-c601-pod-system-vape-kit.html, 6 pages.
Notice of Allowance for Chinese Application No. 201630632827.4, dated Feb. 24, 2017, 2 pages.
Notice of Allowance for Japanese Application No. 2016016955, dated Feb. 14, 2017, 2 pages.
Notice of Allowance for Japanese Application No. 2016016956, dated Feb. 14, 2017, 2 pages.
Notice of Allowance for Japanese Application No. 2017-000313, dated Dec. 19, 2017, 3 pages.
Notice of Issuance for Chinese Application No. 201630370608.3, dated Dec. 30, 2016, 3 pages.
Notice of Reason for Refusal for Japanese Application No. 2018-548027 dated Dec. 10, 2019, 10 pages.
Notice of Reason for Refusal for Japanese Application No. 2018-548374 dated Oct. 1, 2019, 8 pages.
Office Action dated Jun. 1, 2020 for Chinese Application No. 201780019532.1, 46 pages.
Office Action dated May 20, 2020 for Chinese Application No. 201780018952.8, 21 pages.
Office Action for Canadian Application No. 3,018,460, dated Jul. 23, 2019, 6 pages.
Office Action for Chinese Application No. 201630370608.3, dated Nov. 1, 2016, 1 page.
Office Action for Japanese Application No. 2017-000313, dated Aug. 29, 2017, 4 pages.
Office Action dated Oct. 14, 2019 for Chilean Application No. 201802657, 16 pages.
Office Action dated Feb. 17, 2020 for Chilean Application No. 201802640, 15 pages.
Office Action dated Oct. 17, 2019 for Korean Application No. 10-2018-7038106, 17 pages.
Office action dated May 26, 2020 for Japanese Application No. 2018-545821, 8 pages.
Office Action dated Jun. 29, 2020 for Chinese Application No. 201780018542.3, 12 pages.
Office Action dated Mar. 30, 2020 for Korean Application No. 10-2018-7027563, 21 pages.
Office Action dated Feb. 21, 2017 for Russian Application No. 2016505393.
Office Action dated Jan. 13, 2017 for Ukrainian Application No. S201601341, 1 pages.
Office Action dated Nov. 23, 2016 for Mexican Application No. MX/f/2016/002430, 1 pages.
Office Action dated Oct. 6, 2016 for Russian Application No. 2016503052, 2 pages.
Search Report dated Jun. 10, 2019 for Russian Application No. 2018133541, 2 pages.
Search Report dated Aug. 11, 2016 for Great Britain Application No. 1605104.7, 5 pages.
Search Report dated Aug. 16, 2016 for Great Britain Application No. 1605103.9, 4 pages.
Search Report dated Aug. 25, 2016 for Great Britain Application No. 1605100.5, 3 pages.
Search Report dated Aug. 3, 2016 for Great Britain Application 1605106.2, 5 pages.
Search Report dated Feb. 9, 2016 for Great Britain Application No. GB1517088.9, 3 pages.
Search Report dated Jun. 9, 2017 for Great Britain Application No. 1612684.9, 4 pages.
Smoant S8 Ultra-Portable System Kit_Premium Electronic Cigarette by wicked vapor, mailed 2018, found online on Sep. 24, 2018, at https://wicked-vapor.com/products/smoant-s8-ultra-portable-system-kit, 2 pages.
U.S. Appl. No. 16/087,005, filed Sep. 20, 2018, Nettenstrom et al., Inventor(s), 37 pages.
U.S. Appl. No. 16/087,012, filed Sep. 20, 2018, Nettenstrom et al., Inventor(s), 39 pages.
U.S. Appl. No. 16/087,021, filed Sep. 20, 2018, Nettenstrom et al., Inventor(s), 27 pages.
Vincent V., "Renova Vapor Zero vape Pod Kit", mailed May 29, 2018, found online on Sep. 24, 2018, https://www.e-cigarette-forum.com/threads/renova-vapor-zero-vape-pod-kit-hqd-comma-vape-pod-kit-wismec-hiflask-pod-kit.865421/.
Written Opinion of the International Preliminary Examining Authority for Application No. PCT/GB2017/050783, dated Mar. 2, 2018, 6 pages.
U.S. Appl. No. 16/087,019, filed Sep. 20, 2018, Nettenstrom et al., Inventor(s), 243 pages.
Office Action dated Feb. 2, 2021 for Ukraine Application No. 201809441, 11 pages.
Office Action For GB Application No. 1605104.7, dated Apr. 12, 2021, 6 pages.
Office Action For Korean Application No. 2018-7027488, dated Jul. 22, 2021, 20 pages.
Search Report For Japanese Application No. 2018-545824, dated Oct. 9, 2019, 80 pages.
Search Report for Japanese Application No. 2018-548374, dated Sep. 25, 2019, 35 pages.
Search Report dated Nov. 25, 2019 for Japanese Application No. 2018-548027, 26 pages.
Search Report dated Sep. 5, 2019 for Japanese Application No. 2018-545821, 41 pages.

* cited by examiner

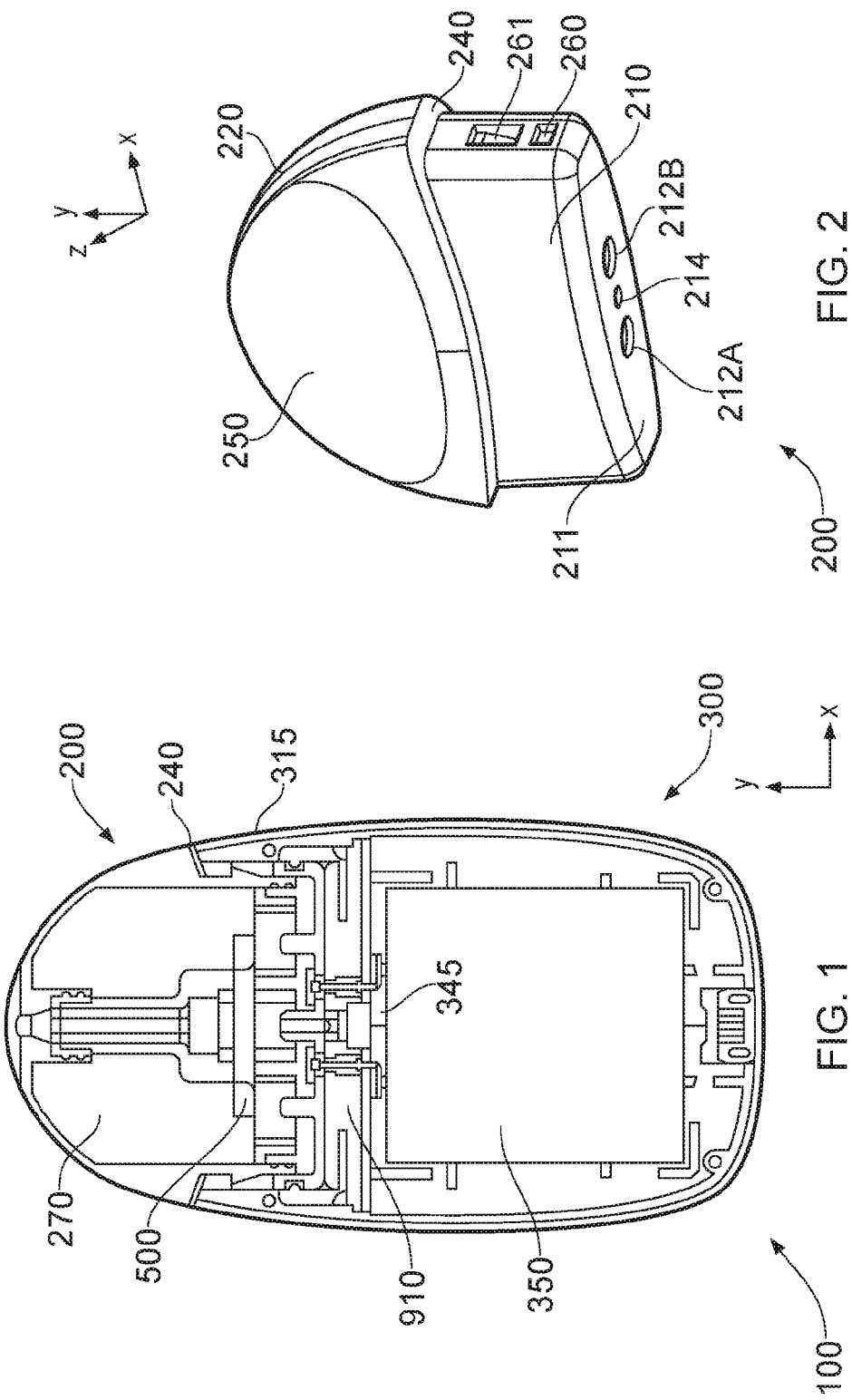

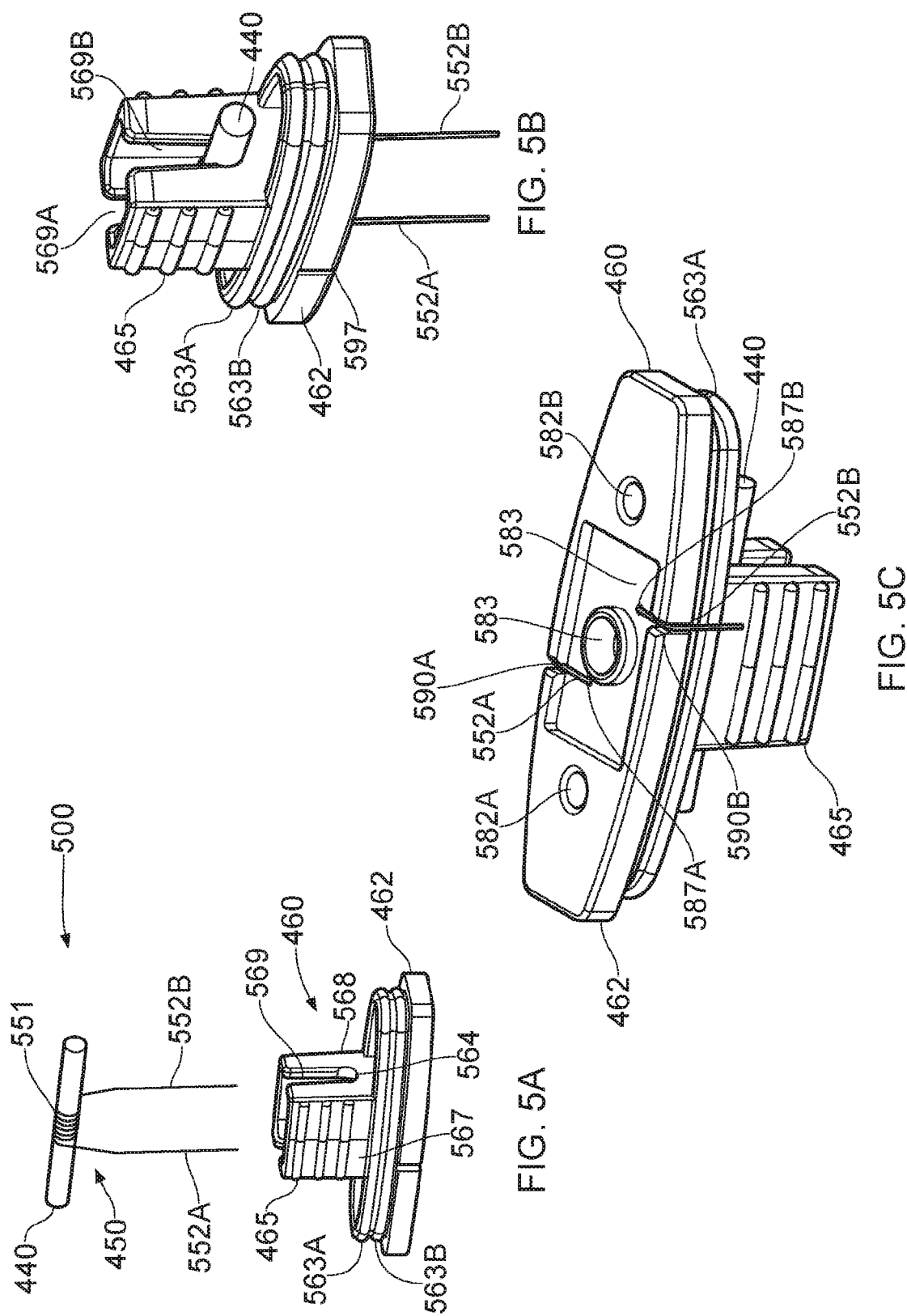

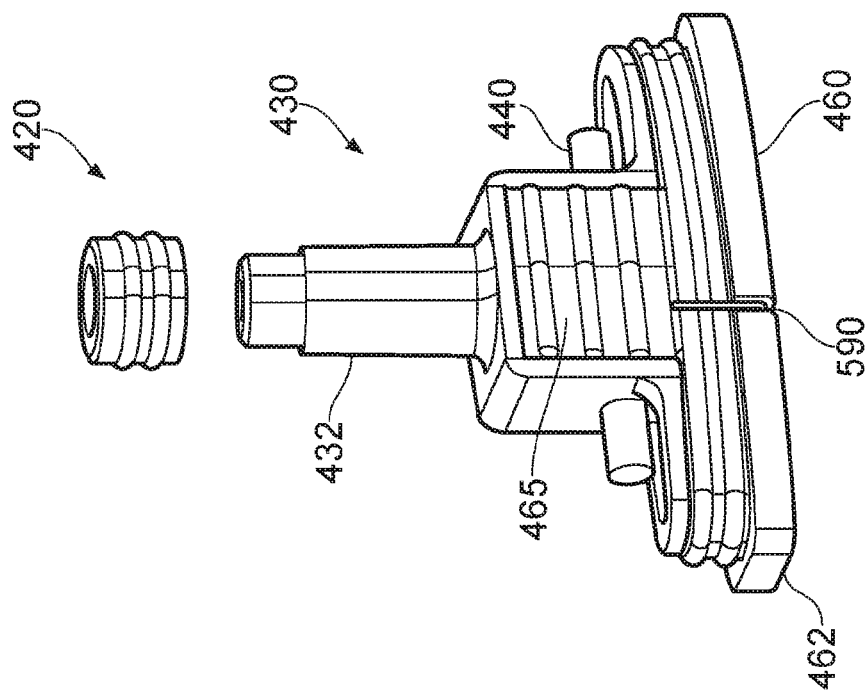
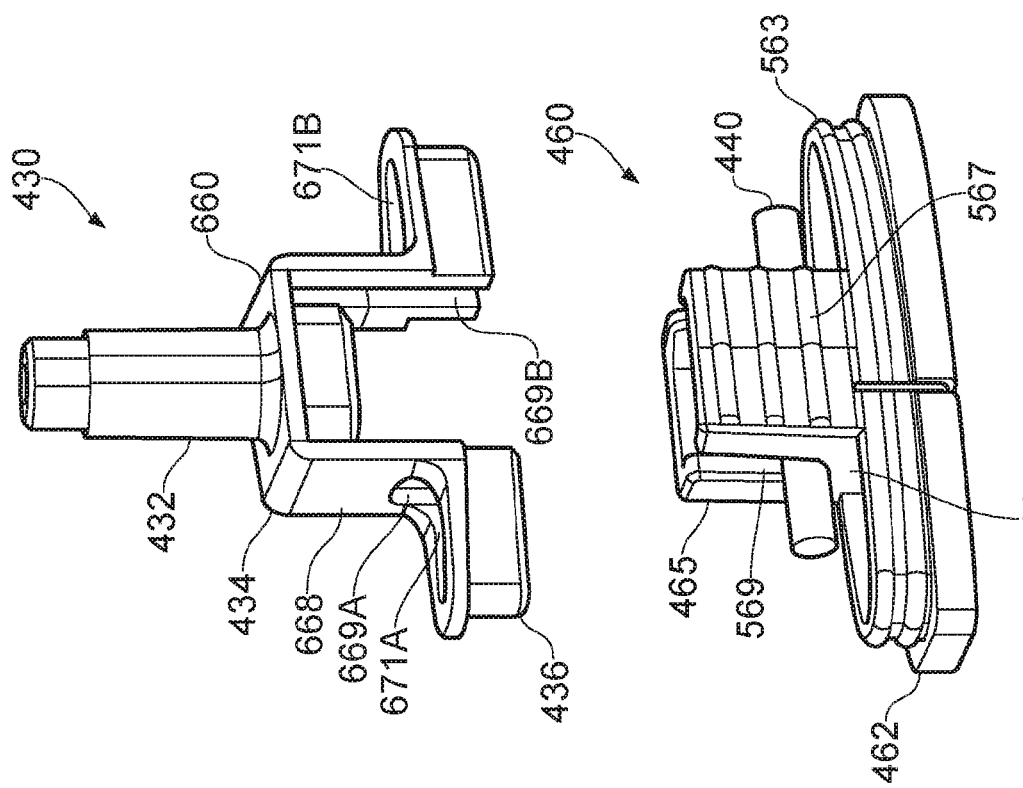

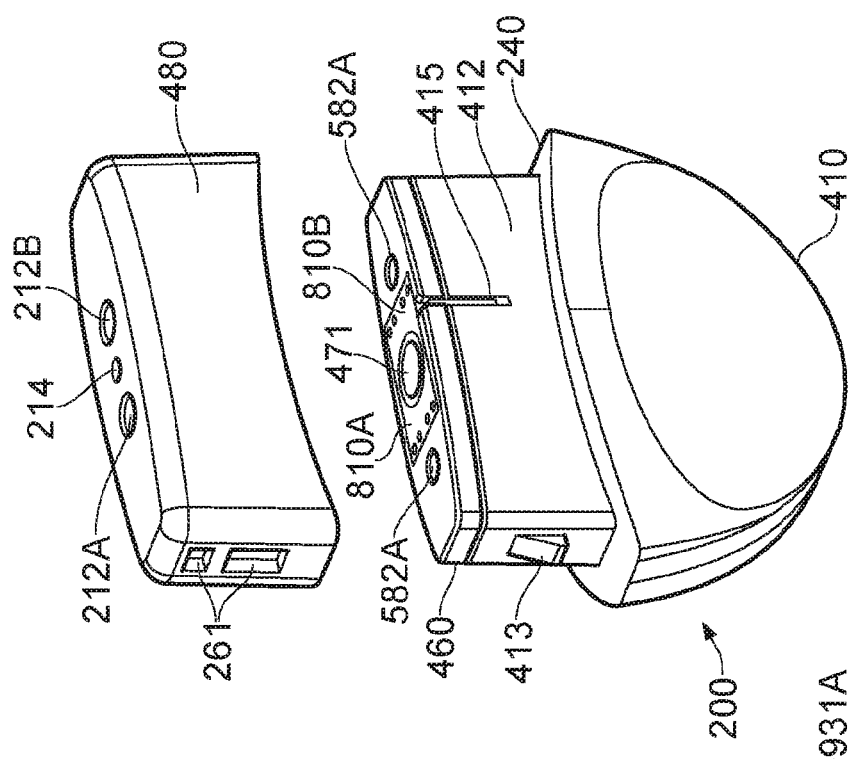
FIG. 8B
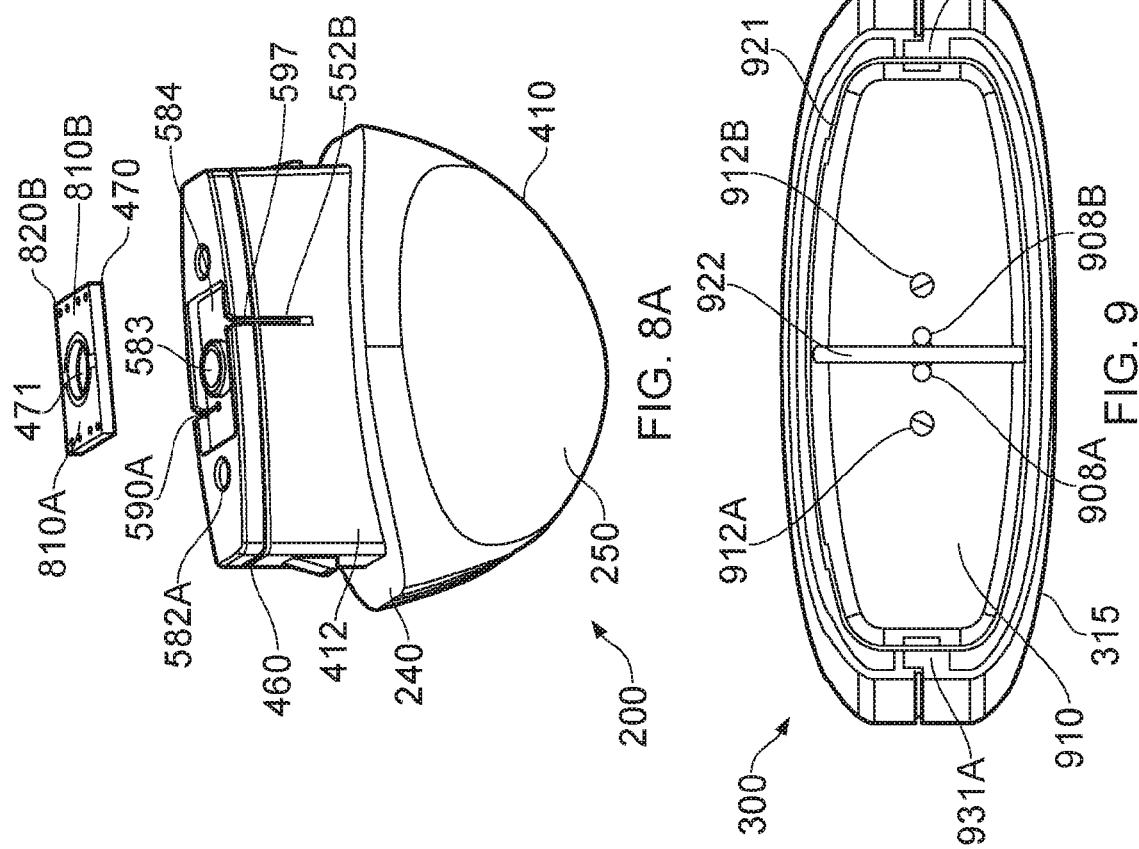
FIG. 8A
FIG. 9

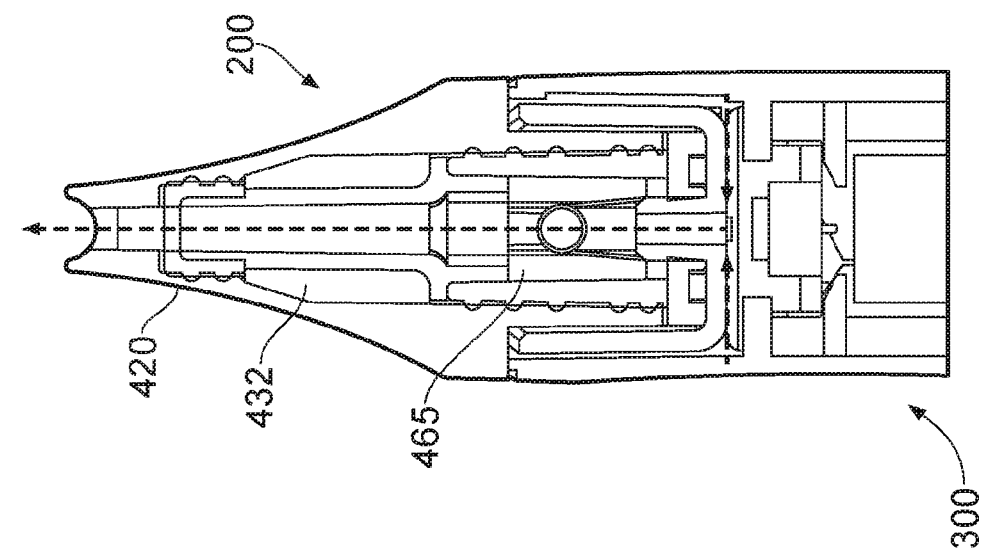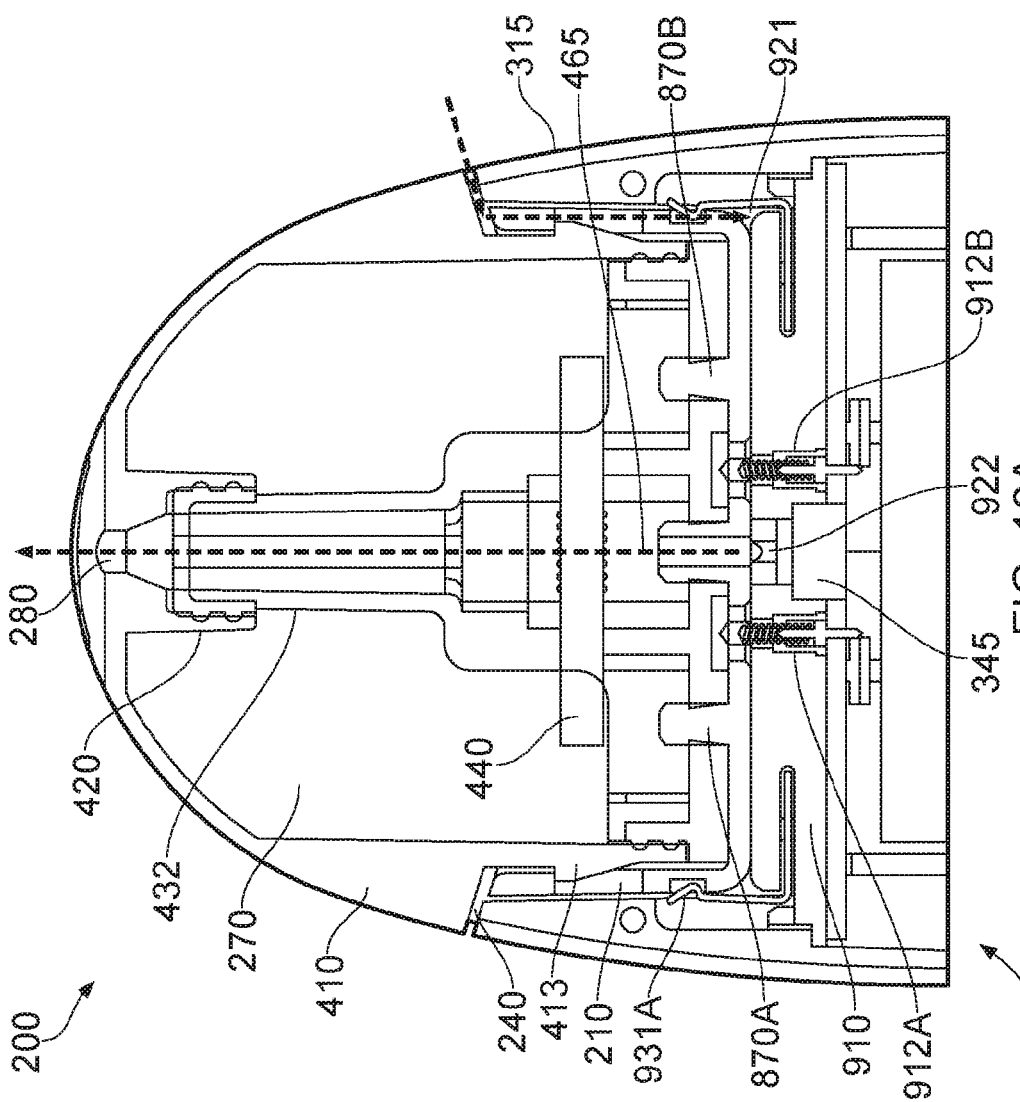

VAPOR PROVISION SYSTEM

PRIORITY CLAIM

The present application is a National Phase entry of PCT Application No. PCT/GB2017/050789, filed Mar. 21, 2017, which claims priority from GB Patent Application No. 1605100.5, filed Mar. 24, 2016, and GB Patent Application No. 1612684.9, filed Jul. 21, 2016, each of which is hereby fully incorporated herein by reference.

FIELD

The present disclosure relates to a vapor provision system, e.g. an e-cigarette, as well as to various components thereof, such as a cartridge, cartomizer or atomizer.

BACKGROUND

Many electronic vapor provision systems, such as e-cigarettes and other electronic nicotine delivery systems, are formed from two main components—a cartomizer and a control unit. The cartomizer generally includes a reservoir of liquid and an atomizer for vaporizing the liquid. The atomizer is often implemented as an electrical (resistive) heater, such as a coil of wire. The control unit generally includes a battery for supplying power to the atomizer. In operation, the control unit may be activated, for example by detecting when a user inhales on the device and/or when the user presses a button, to provide electrical power from the battery to the heater. This activation causes the heater to vaporize a small amount of liquid from the reservoir, which is then inhaled by the user.

This type of e-cigarette therefore generally incorporates two consumables, firstly the liquid to be vaporized, and secondly power in the battery. Regarding the former, once the reservoir of liquid has been exhausted, the cartomizer may be discarded to allow replacement with a new cartomizer. Regarding the latter, the control unit may provide some form of electrical connector for receiving power from an external source, thereby allowing the battery within the e-cigarette to be re-charged.

Although e-cigarettes have developed rapidly over the past few years, there remain areas where it is desirable to improve the operability and user experience for such devices.

SUMMARY

Some embodiments provide a cartomizer for a vapor provision system, the cartomizer including: a container for holding a reservoir of free liquid to be vaporized; an atomizing chamber; a porous wick (e.g. a fibrous wick or comprising a porous solid, e.g. ceramic, material) extending from inside the container, through an aperture in a wall of the atomizing chamber, to inside the atomizing chamber in order to convey the liquid from the reservoir to the inside of the atomizing chamber for vaporization; and a resilient seal contained in said aperture to restrict/prevent the liquid from entering the atomizing chamber from the reservoir except by travelling along the wick.

BRIEF DESCRIPTION OF THE DRAWINGS

Various embodiments of the disclosure will now be described in detail by way of example only with reference to the following drawings:

FIG. 1 is a cross-section through an e-cigarette comprising a cartomizer and a control unit in accordance with some embodiments of the disclosure.

FIG. 2 is an isometric external view of the cartomizer of the e-cigarette of FIG. 1 in accordance with some embodiments of the disclosure.

FIGS. 5A, 5B and 5C illustrate the wick/heater assembly being fitted into the cartomizer plug in accordance with some embodiments of the disclosure.

FIGS. 6A and 6B illustrate the inner frame and the vent seal being fitted into the cartomizer plug in accordance with some embodiments of the disclosure.

FIGS. 8A and 8B illustrate the PCB and end cap being fitted to the other components to complete the formation of the cartomizer in accordance with some embodiments of the disclosure.

FIG. 9 is a top view looking down onto the control unit of the e-cigarette of FIG. 1 in accordance with some embodiments of the disclosure.

FIGS. 10A and 10B are cross-sections respectively (a) from side to side, and (b) from front to back, showing the airflow through the e-cigarette of FIG. 1 in accordance with some embodiments of the disclosure.

DETAILED DESCRIPTION

Figure 3:
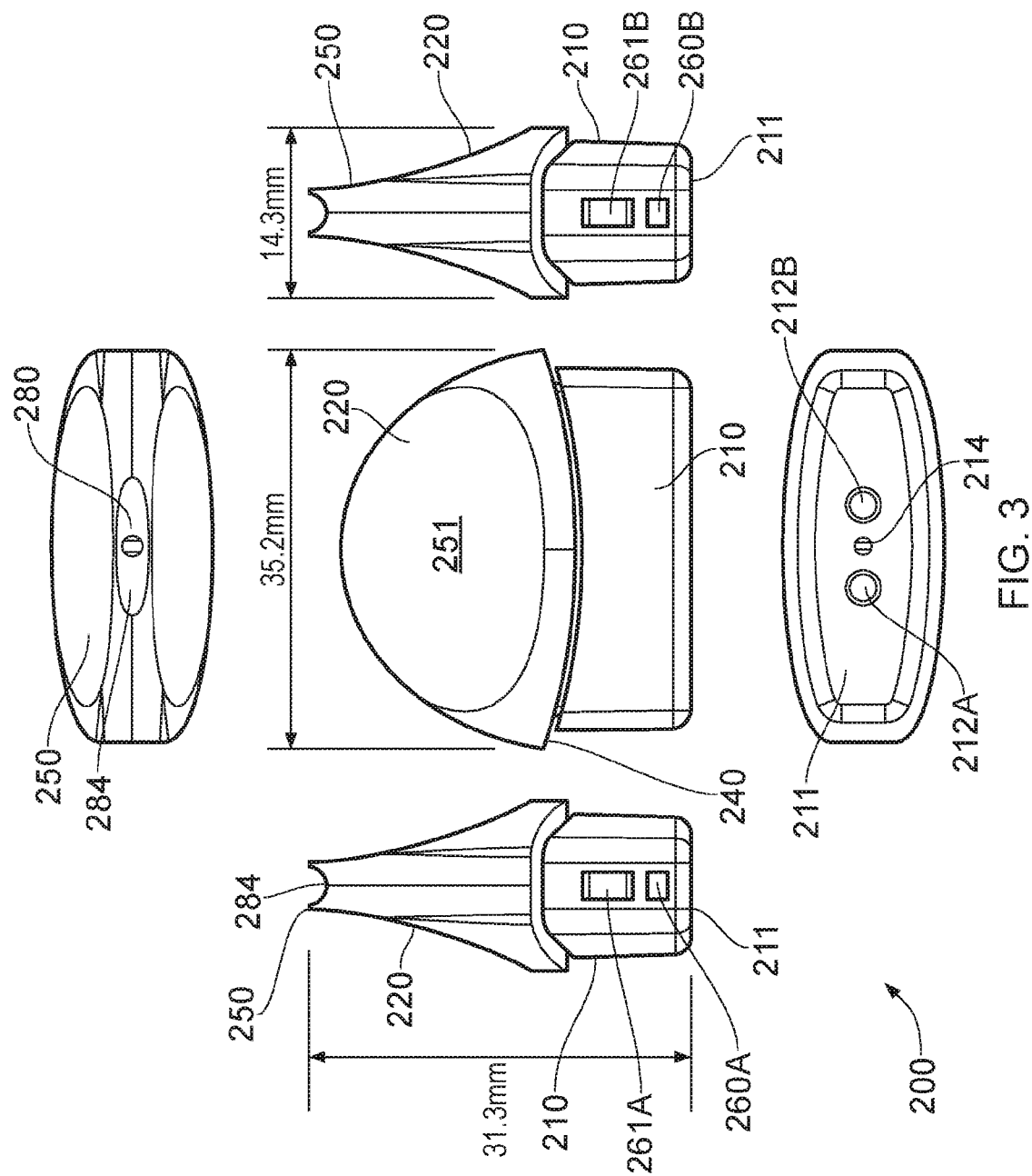
FIG. 3 is a collection of five external views of the cartomizer of FIG. 2 in accordance with some embodiments of the disclosure. In particular, the bottom view shows the cartomizer from underneath, the top view shows the cartomizer from above, the central view shows a face view of the cartomizer (from front or back), and on either side of the central view are respective side views of the cartomizer.

FIG. 1 is a cross-section through an e-cigarette 100 in accordance with some embodiments of the disclosure. The e-cigarette 100 comprises two main components, namely a cartomizer 200 and a control unit 300. As discussed in more detail below, cartomizer 200 includes a chamber 270 containing a reservoir of liquid, a heater to act as an atomizer or vaporizer, and a mouthpiece. The liquid in the reservoir (sometimes referred to as the e-liquid) typically includes nicotine in an appropriate solvent, and may include further constituents, for example, to aid aerosol formation, and/or for additional flavoring. The cartomizer 200 further includes a wick/heater assembly 500, which includes a wick or similar facility to transport a small amount of liquid from the reservoir to a heating location on or adjacent the heater. The control unit 300 includes a re-chargeable cell or battery 350 to provide power to the e-cigarette 100, a printed circuit board (PCB) for generally controlling the e-cigarette 100 (not shown in FIG. 1), and a microphone 345 for detecting a user inhalation (via a pressure drop). When the heater receives power from the battery 350, as controlled by the PCB in response to the microphone 345 detecting a user puff on the e-cigarette 100, the heater vaporizes the liquid from the wick and this vapor is then inhaled by a user through the mouthpiece.

For ease of reference, the x and y axes are marked in FIG. 1. The x axis will be referred to herein as the width of the device 100 (from side to side), while the y axis will be referred to herein as the height axis, where the cartomizer 200 represents the upper portion of the e-cigarette 100 and the control unit 300 represents the lower portion of the e-cigarette 100. Note that this orientation reflects how a user holds the e-cigarette 100 during normal operation of the device 100, given that the wick is located in the lower part of the reservoir in the cartomizer 200. Therefore holding the e-cigarette 100 in this orientation ensures that the wick is in contact with liquid at the bottom of the reservoir.

We further assume a z axis (not shown in FIG. 1) which is perpendicular to the x and y axes shown in FIG. 1. The z axis will be referred to herein as the depth axis. The depth of e-cigarette 100 is significantly less than the width of the e-cigarette 100, thereby resulting in a generally flat or planar configuration (in the x-y plane). Accordingly, the z axis can be considered as extending from face to face of the e-cigarette 100, where one face may be regarded (arbitrarily) as the front face of the e-cigarette 100 and the opposing face as the back face of the e-cigarette 100.

The cartomizer 200 and the control unit 300 are detachable from one another by separating in a direction parallel to the y-axis, but are joined together when the device 100 is in use so as to provide mechanical and electrical connectivity between the cartomizer 200 and the control unit 300. When the e-liquid in cartomizer reservoir 270 has been depleted, the cartomizer 200 is removed and a new cartomizer is attached to the control unit 300. Accordingly, the cartomizer 200 may sometimes be referred to as the disposable portion of the e-cigarette 100, while the control unit 300 represents the re-usable portion.

FIG. 2 is an isometric external view of the cartomizer 200 of the e-cigarette 100 of FIG. 1 in accordance with some embodiments of the disclosure. This external view confirms that the depth of the cartomizer 200 (and the e-cigarette 100 as a whole), as measured parallel to the z axis, is significantly less than the width of the cartomizer 200 (and the e-cigarette 100 as a whole), as measured parallel to the x axis. Note that overall, the external appearance of the cartomizer 200 is relatively smooth and uncluttered.

The cartomizer 200 comprises two main portions (at least from an external viewpoint). In particular, there is a lower or base portion 210 and an upper portion 220. The upper portion 220 provides the mouthpiece 250 of the e-cigarette 100, as described in more detail below. When the cartomizer 200 is assembled with the control unit 300, the base portion 210 of the cartomizer 200 sits within the control unit 300, and hence is not externally visible, whereas the upper portion 220 of the cartomizer 200 protrudes above the control unit 300, and hence is externally visible. Accordingly, the depth and width of the base portion 210 are smaller than the depth and width of the upper portion 220, to allow the base portion 210 to fit within the control unit 300. The increase in depth and width of the upper portion 220 compared with the base portion 210 is provided by a lip or rim 240. When the cartomizer 200 is inserted into the control unit 300, this lip or rim 240 abuts against the top of the control unit 300.

As shown in FIG. 2, the side wall of base portion 210 includes a notch or indentation 260 for receiving a corresponding latching member from the control unit 300. The opposite side wall of the base portion 210 is provided with a similar notch or indentation to likewise receive a corresponding latching member from the control unit 300. It will be appreciated that this pair of notches 260 on the base portion 200 (and the corresponding latching members of the control unit 300) provide a latch or snap fit connection for securely retaining the cartomizer 200 within the control unit 300 during operation of the device 100. Adjacent to the notch 260 is a further notch or indentation 261, which is utilized in the formation of the cartomizer 200, as described in more detail below.

As also shown in FIG. 2, the bottom wall 211 of the base portion 210 includes two larger holes 212A, 212B on either side of a smaller hole 214 for air inlet. The larger holes 212A and 212B are used to provide positive and negative electrical connections from the control unit 300 to the cartomizer 200. Thus when a user inhales through the mouthpiece 250 and the device 100 is activated, air flows into the cartomizer 200 through the air inlet hole 214. This incoming air flows past the heater (not visible in FIG. 2), which receives electrical power from the battery 350 in the control unit 300 so as to vaporize liquid from the reservoir (and more especially from the wick). This vaporized liquid is then incorporated or entrained into the airflow through the cartomizer, and hence is drawn out of the cartomizer 200 through mouthpiece 250 for inhalation by the user.

FIG. 3 is a collection of five external views of the cartomizer 200 of FIG. 2 in accordance with some embodiments of the disclosure invention. In particular, the bottom view shows the cartomizer 200 from underneath, the top view shows the cartomizer 200 from above, the central view shows a face view of the cartomizer 200 (from front or back), and on either side of the central view are respective side views of the cartomizer 200. Note that since the cartomizer 200 is symmetric front/back (i.e. with respect to the z axis), the front face of the cartomizer 200 and the back face of the cartomizer 200 both correspond to the central view of FIG. 3. In addition, the cartomizer 200 is also symmetric in the width direction (i.e. with respect to the x axis), hence the two side views to the left and right of the central view are the same.

FIG. 3 illustrates the various features of the cartomizer 200 already discussed above with respect to FIG. 2. For example, the central view clearly shows the top portion 220 and the bottom portion 210 of the cartomizer 200. The lower view shows the bottom wall of the base portion 211, including the two larger holes 212A and 212B, which are used to provide positive and negative electrical connections from the control unit 300 to the cartomizer 200, plus the smaller hole 214 for air inlet into the cartomizer 200. In addition, the two side views show the two notches in each side wall, an upper notch 261A, 261B, and a lower notch 260A, 260B, the latter being used to fasten the cartomizer 200 to the control unit 300.

The top view further shows a hole 280 in the mouthpiece 250 which represents the air outlet from the cartomizer 200. Thus in operation, when a user inhales, air enters the cartomizer 200 at the bottom through inlet 214, flows through the atomizer, including past the heater, where it acquires vapor, and then travels up the center of the cartomizer 200 to exit through air outlet 280.

FIG. 3 provides dimensions of the cartomizer 200, showing a maximum height (in the y direction) of 31.3 mm, a maximum width (in the x direction) of 35.2 mm, and a maximum depth of 14.3 mm (parallel to the z direction). Note that these maximum width and depth measurements relate to the upper portion 220 of the cartomizer 200; the width and depth of the base portion 210 are somewhat smaller, in order to allow the base portion to be received into the control unit 300. The difference in width and depth between the upper portion 220 and the base portion 210 is accommodated by the rim or flange 240, as described above.

It will be appreciated that the dimensions shown in FIG. 3 are provided by way of example only, and may vary between embodiments. Nevertheless, the dimensions given do confirm that the e-cigarette 100, including the cartomizer 200, has an approximately flat or planar shape, with one relatively small dimension (the z direction) perpendicular to the planar shape. This planar shape is extended by the control unit 300, which in effect extends the height (y dimension of the cartomizer), but shares substantially the same width and depth.

FIG. 3 also gives a clear indication of the size and shape of the mouthpiece 250. In contrast to many e-cigarettes, which provide a circular mouthpiece akin to a straw or conventional cigarette, the mouthpiece 250 has a very different and distinctive shape. In particular, the mouthpiece 250 comprises a pair of large, relatively flat, opposing faces. One of these mouthpiece faces is denoted as face 251 in the central view of FIG. 3, and there is a corresponding, opposing face to the rear of the device. (Note that the labeling of front and back for the cartomizer 200 is arbitrary, since it is symmetric with respect to the z axis, and can be fitted either way around onto the control unit 300.)

The front and rear faces 251 provide relatively large surfaces onto which the lips of a user can be placed. For example, we can consider the front face to provide a surface for engaging the upper lip, and the rear face to provide a surface for engaging the lower lip. In this configuration, we can regard the height (y axis) of the e-cigarette 100 defining a longitudinal axis extending away from the user's mouth, the width of the e-cigarette 100 (the x axis) as running parallel to the line between a user's upper and lower lips, and the depth of the e-cigarette 100 (the z axis) as running parallel to the direction of separation of the user's upper and lower lips.

The height of the front and rear mouthpiece faces 251 (approximately 17 mm in the particular embodiment of FIG. 3) is broadly comparable to the typical thickness of a lip, and therefore large enough to readily accommodate in this direction a lip placed on the surface. Similarly, the width of the front and rear mouthpiece faces 251 (approximately 28 mm in the particular embodiment of FIG. 3) represents a significant proportion (very approximately half) of the typical width of lips (from one side of the mouth to the other).

This shape and sizing of the mouthpiece 250 allows the lips of user to engage the mouthpiece 250 for inhalation with much less distortion from the normal resting position of the mouth—e.g. there is no need to purse the lips, as for a straw or conventional cigarette having a small circular mouthpiece. This makes using the mouthpiece 250 of the e-cigarette 100 a more relaxing experience, and also may help to ensure a more consistent seal between the mouth and the mouthpiece 250.

In addition, e-cigarette 100 (like many other e-cigarettes) uses a sensor to detect airflow through the device 100, i.e. a user puff, which can then trigger operation of the heater to vaporize the liquid. The device 100 has to discriminate between the airflow caused by a user puff, and other forms of airflow or pressure changes that arise due to other actions or circumstances—e.g. movement of the e-cigarette 100 through the air, being on a railway train which enters a tunnel, etc. Having a consistent seal between the mouth and the mouthpiece 250 can help the device provide better discrimination of an actual inhalation, and so reduce the risk of unintentional activation of the heater.

Furthermore, some e-cigarettes use sensor measurements of the airflow through the device not only to initiate activation of the heater, but also to provide dynamic control of the heater (or other components of the e-cigarette). For example, as the measured airflow increases, the heater may be provided with more power, firstly to compensate for the cooling effect of the increased airflow, and/or secondly to vaporize more liquid into the increased airflow. Having a consistent seal between the mouth and the mouthpiece 250 can again help to improve the reliability and accuracy of this dynamic control.

In addition, with reference to the side views of FIG. 3, it can be seen that the front and back faces 251 of the mouthpiece 250 generally slope towards one another at the top of the device. In other words, the depth or separation of the opposing faces (as measured in the z direction) decreases towards the air outlet hole 280 (i.e. as the y axis increases). This slope is relatively gentle—approximately 15 degrees with respect to the y axis. This incline helps to provide a natural and comfortable engagement between the faces 251 of the mouthpiece 250 and the lips of a user.

As can be seen in FIG. 3, the front and back faces 251 do not converge completely at the top of the mouthpiece 250, but rather overhang to provide a small valley 284 which extends in the x-direction of the device 100. The opening 280, which allows air and vapor to exit from the cartomizer 200, is formed in the center of this valley 284. Having this small overhang, so that the mouthpiece opening 280 is located in the groove or valley 284, helps to protect the mouthpiece 250 opening from physical contact, and hence from potential damage and dirt.

Figure 4:
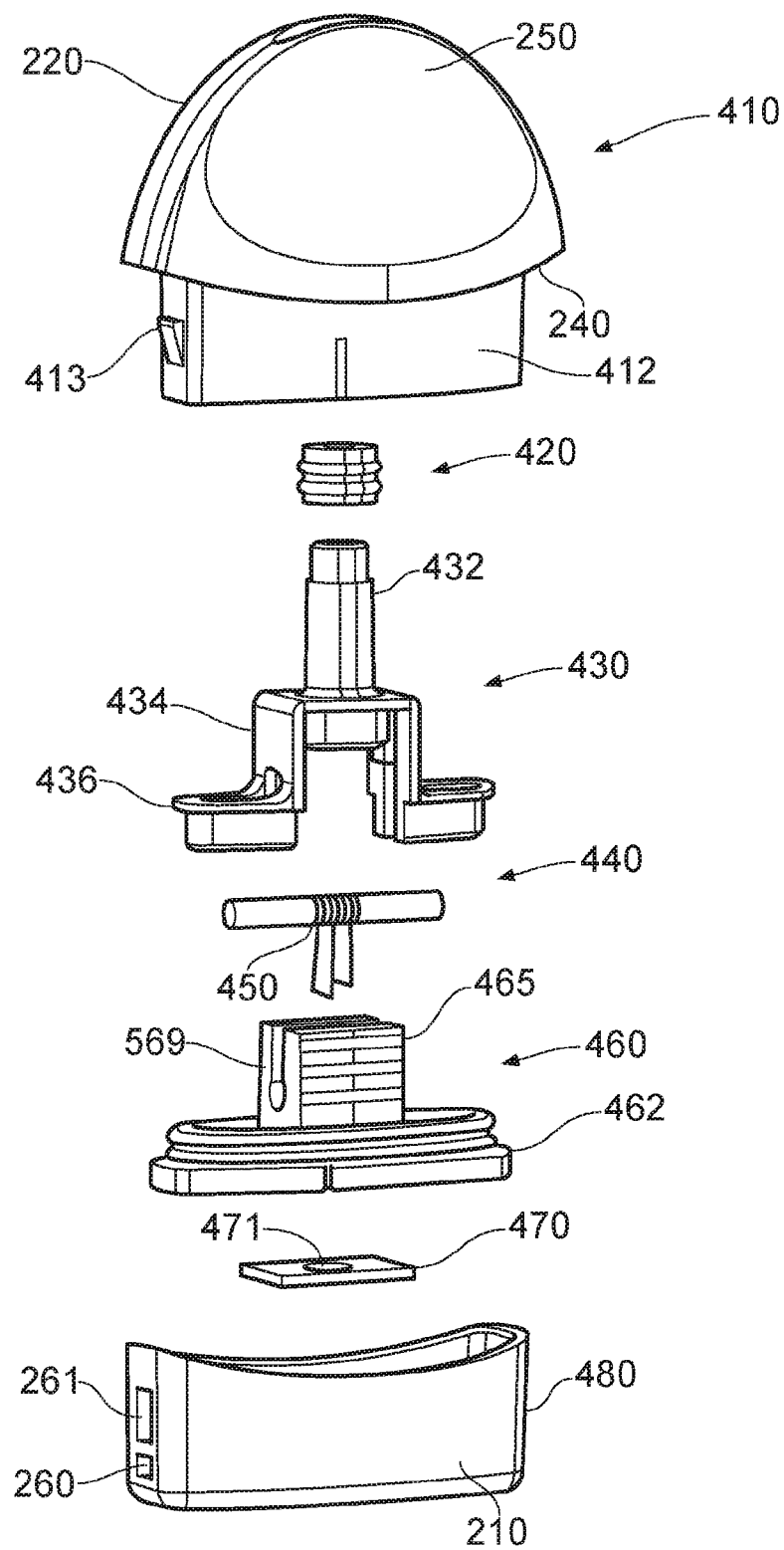
FIG. 4 is an exploded view of the cartomizer of the e-cigarette of FIG. 1 in accordance with some embodiments of the disclosure.

FIG. 4 is an exploded view of the cartomizer 200 of the e-cigarette 100 of FIG. 1 in accordance with some embodiments of the disclosure. The cartomizer 200 includes a shell 410, a vent seal 420, an inner frame 430, a heating coil 450 located on a wick 440, a primary seal 460 (also referred to as the cartomizer plug), a printed circuit board (PCB) 470 and an end cap 480. The view of FIG. 4 shows the above components exploded along the longitudinal (height or y) axis of the cartomizer 200.

The cap 480 is formed from substantially rigid plastic such as polypropylene and provides the base portion 210 of the cartomizer 200. The cap 480 is provided with two holes 260, 261 on each side (only one side is visible in FIG. 4, but the side which is not visible is the same as the side that is visible). The lower hole 260 is for latching the cartomizer 200 to the control unit 300, while the upper hole 261 is for latching the end cap 480 to the shell 410. As described in more detail below, latching the cap 480 and the shell 410 in effect completes the assembly of the cartomizer 200, and retains the various components shown in FIG. 4 in the correct position.

Above the end cap is located the PCB 470, which includes a central air hole 471 to allow air to flow through the PCB 470 into the atomizer (the end cap 480 is likewise provided with a central air hole, not visible in FIG. 4) to support this air flow into the atomizer. In accordance with some embodiments, the PCB 470 does not contain any active electrical components, but rather provides a circuit or conductive path between the control unit 300 and the heater 450.

Above the PCB 470 is located the primary seal 460, which has two main portions, an upper portion which defines (in part) an atomizer chamber 465, and a lower portion 462 which acts as an end seal for the reservoir 270. Note that in the assembled cartomizer 200, the reservoir of e-liquid is located around the outside of the atomizer chamber 465, and the e-liquid is prevented from leaving the cartomizer 200 (at least in part) by the lower portion 462 of the cartomizer plug 460. The cartomizer plug 460 is made from a material that is slightly deformable. This allows the lower portion 462 to be compressed a little when inserted into the shell 410, and hence provide a good seal to retain the e-liquid in reservoir 270.

Two opposing side walls of the atomizer chamber 465 are provided with respective slots 569 into which the wick 440 is inserted. This configuration thereby ensures that the heater 450, which is positioned on the wick 440, is located near the bottom of the atomizer chamber 465 to vaporize liquid introduced into the atomizer chamber 465 by wick 440. In some embodiments, the wick 440 is made of glass fiber rope (i.e. filaments or strands of glass fiber twisted together), and the heater coil 450 is made of nichrome (an alloy of nickel and chromium). However, various other types of wick and heater are known and could be used in the cartomizer 200, such as a wick made out of porous ceramic, and/or some form of planar heater (rather than a coil). Note that although FIG. 4 suggests that the heater coil 450 has a loop of wire dropping down from the wick 440 at each end, in practice there is just a single lead at each end (as described in more detail below).

The cartomizer plug 460 and the wick/heater assembly are surmounted by the inner frame 430, which has three main sections. The inner frame 430 is substantially rigid, and may be made of a material such as polybutylene terephthalate. The lowermost section 436 of the inner frame 430 covers the lower portion 462 of the cartomizer plug 460, while the middle section 434 completes the atomizer chamber 465 of the cartomizer plug 460. In particular, the inner frame 430 provides the top wall of the atomizer chamber, and also two side walls that overlap with the two side walls of the atomizing chamber 465 of the cartomizer plug 460. The final section of the inner frame is an airflow tube 432 that leads upwards from the top wall of the atomizing chamber (part of the middle section 434) and connects with the mouthpiece hole 280. In other words, tube 432 provides a passage for vapor produced in the atomizing chamber 465 to be drawn out of the e-cigarette 100 and inhaled through mouthpiece 250.

Since the inner frame 430 is substantially rigid, the vent seal 420 is provided at (inserted around) the top of the airflow tube 432 to ensure a proper seal between the inner frame 430 and the mouthpiece exit hole 280. The vent seal 420 is made of a suitably deformable and resilient material such as silicone. Lastly, the shell 410 provides the external surface of the upper portion 220 of the cartomizer 200, including the mouthpiece 250, and also the lip or flange 240. The shell 410, like the end cap, is formed of a substantially rigid material, such as polypropylene. The lower section 412 of the shell 410 (i.e. below the lip 240) sits inside the end cap 480 when the cartomizer 200 has been assembled. The shell is provided with a latch tab 413 on each side to engage with hole 261 on each side of the end cap 480, thereby retaining the cartomizer 200 in its assembled condition.

In the example shown in FIG. 4, the top surface of the latch tab 413 is horizontal—i.e. in the x-z plane, perpendicular to the wall of the shell 410. In some implementations, this top surface of latch tab 413 slopes downwards and inwards towards the shell 410, for example at an angle of up to 45 degrees to the horizontal—e.g. at an angle of 10 degrees. This slope can help to give more secure latching between the shell 410 and the end cap 480.

The airflow passage through the cartomizer 200 enters a central hole in the cap 480 (not visible in FIG. 4) and then passes through a hole 471 in the PCB 470. The airflow next passes up into the atomizer chamber 465, which is formed as part of the cartomizer plug 460, flows around the wick 440 and heater assembly 500 and through the tube 432 of the inner frame 430 (and through vent seal 420), and finally exits through the hole 280 in the mouthpiece 250.

The reservoir 270 of e-liquid is contained in the space between this airflow passage and the outer surface of the cartomizer 200. Thus shell 410 provides the outer walls (and top) of the housing for the reservoir 270, while the lower section 436 of the inner frame 430 in conjunction with the base portion 462 of the primary seal 460 and end cap 480 provide the bottom or floor of the housing for the reservoir 270 of e-liquid. The inner walls of this housing are provided by the atomizing chamber 465 of the primary seal 460, in cooperation with the middle section 434 of the inner frame 430, and also the airflow tube 432 of the inner frame 430 and the vent seal 420. In other words, the e-liquid is stored in the reservoir space between the outer walls and the inner walls. However, the e-liquid should not penetrate inside the inner walls, into the airflow passage, except via wick 440, otherwise there is a risk that liquid would leak out of the mouthpiece hole 280.

The capacity of this space is typically of the order of 2 ml in accordance with some embodiments, although it will be appreciated that this capacity will vary according to the particular features of any given design. Note that unlike for some e-cigarettes, the e-liquid reservoir 270 is not provided with any absorbent material (such as cotton, sponge, foam, etc.) for holding the e-liquid. Rather, the reservoir chamber only contains the liquid, so that the liquid can move freely around the reservoir 270. This has certain advantages, such as generally supporting a larger capacity, and also making the filling procedure less complex. One potential disadvantage with having a free liquid in the reservoir 270 (i.e. not holding the liquid in a sponge or other absorbent structure) is that the liquid can flow more easily, and hence might be more likely to leak in an undesirable manner from the reservoir 270 into the airflow passage. However, such leakage is generally prevented by the vent seal 420 and the primary seal 460.

FIGS. 5A, 5B and 5C illustrate the wick/heater assembly being fitted into the cartomizer plug 460 in accordance with some embodiments of the disclosure. The wick/heater assembly 500 is formed from the heater wire 450 and the wick 440. As noted above, the wick 440 comprises glass fibers formed into a generally cylindrical or rod shape. The heater 450 comprises a coil of wire 551 wound around the wick 440. At each end of the coil 551 there is a contact wire 552A, 552B, which together act as the positive and negative terminals to allow the coil to receive electrical power.

As visible in FIG. 5A, the primary seal 460 includes the base portion 462 and the atomizing chamber 465. The base portion is provided with two outwardly directed ribs. When the shell 410 is fitted over the base portion, these ribs are compressed slightly in order to fit inside the shell 410. This compression and the resulting slight resilient deformation of the ribs helps to ensure a good seal for the e-liquid at the base of the cartomizer reservoir 270.

Also visible in FIG. 5A, the atomizing chamber 465 comprises four walls in a rectangular arrangement, a pair of opposing side walls 568, and a pair of opposing front and back walls 567. Each of the opposing side walls 568 includes a slot 569 which has an open end at the top (and in the center) of the side wall, and a closed end 564 relatively near the bottom of the atomizing chamber 465—i.e. the two slots 569 extend more than halfway down their respective side walls 568.

Referring now to FIG. 5B, this shows the wick/heater assembly 500 now fitted into the atomizing chamber 465 of the cartomizer plug 460. In particular, the wick/heater assembly is positioned so that it extends between, and protrudes out of, the two opposing slots 569A, 569B. The wick 440 is then lowered until it reaches the closed end 564 of each slot 569A, 569B. Note that in this position, the coil 551 is located entirely in the atomizing chamber 465—it is only the wick itself 440 that extends out of the slots into the reservoir area 270. It will be appreciated that this arrangement allows the wick to draw e-liquid from the reservoir 270 into the atomizing chamber 465 for vaporization by the wire heater coil 551. Having the wick 440 located near the bottom of the atomizing chamber 465, and more particularly also near the bottom of the reservoir 270, helps to ensure that the wick 440 retains access to liquid in the reservoir 270 even as the e-liquid is consumed, and hence the level of the e-liquid in the reservoir 270 drops. FIG. 5B also shows the heater contact wires 552A, 552B extending below the primary seal 460.

FIG. 5C illustrates the underside of the base portion 462 of the primary seal 460. This view shows that the base portion 462 includes two holes 582A, 582B, which are used for filing the reservoir 270 with e-liquid, as described in more detail below. The underside further includes a rectangular indentation 584 for receiving the PCB 470. A central hole 583 is provided in this indentation 584 to provide an air passage from underneath (and outside) the cartomizer 200 into the atomization (vaporization) chamber 465. It will be appreciated that after assembly, this central hole 583 in the cartomizer plug 460 is aligned with the corresponding central hole 471 in the PCB 470.

There are also two much smaller holes 587A, 587B formed in the rectangular indentation 584 of the lower portion of the cartomizer plug 460, one on either side of the central hole 583. The contact wires 552A and 552B extend downwards from the heater 450 and pass respectively through these two holes, 587A, 587B, in order to exit the vaporizing chamber 465.

A slit 590A, 590B is formed in each of the front and back walls of the rectangular indentation 584. After extending through the two holes 587A, 587B, each contact wire from the heater is bent flat onto the underside of the cartomizer plug 460, and then leaves the rectangular indentation via the respective slits 590A, 590B. Thus contact wire 552A passes out of the atomizing chamber 465 through hole 587A, and then exits the rectangular indentation 584 via slot 590A; likewise, contact wire 552B passes out of the atomizing chamber 465 through hole 587B, and then exits the rectangular indentation 584 via slot 590B. The remaining portion of each wire 552A, 552B is then bent upwards towards the atomizing chamber 465 in order to sit within a respective groove 597 in the cartomizer plug 460 (see FIG. 5B). In some examples there may not be respective grooves 597 in the cartomizer plug 460 and the remaining portions of the each wire 552A, 552B may instead be simply bent to run alongside the side of cartomizer plug 460.

FIGS. 6A and 6B illustrate the inner frame and the vent seal being fitted into the cartomizer plug 460 in accordance with some embodiments of the disclosure. Thus as previously described, the inner frame 430 comprises a base section 436, a middle section 434 and air tube 432 located at the top of the inner frame 430. The base section 436 contains two slots 671A, 671B extending in a horizontal sideways direction (parallel to the x axis). As the base section 436 of the inner frame 430 is lowered down past the atomizing chamber 465, the portions of the wick 440 that extend out from each side of the atomizing chamber 465 pass through these slots 671A, 671B, thereby allowing the base section 436 of the inner frame 430 to be lowered further until it is received in the lower portion 462 of the cartomizer plug 460.

As noted above, the middle section 434 of the inner frame 430 complements and completes the atomizing chamber 465 of the cartomizer plug 460. In particular, the middle section provides two opposing side walls 668 and a top wall or roof 660. The latter closes the top of the atomizing chamber 465, except in respect of the air tube 432 which extends up from the atomizing chamber 465 to the exit hole 280 of the mouthpiece 250.

Each of the opposing side walls 668 includes a slot 669A, 669B which extends upwards (parallel to the y axis) from the bottom of the side wall to the closed end of the respective slot. Accordingly, as the base section 436 of the inner frame 430 is lowered down past the atomizing chamber 465, the portions of the wick 440 that extend out from each side of the atomizing chamber 465 pass through these slots 669A, 669B (in addition to slots 671A, 671B). This therefore allows the side walls 668 of the inner frame 430 to overlap the side walls 568 of the cartomizer plug 460. Further downward movement of the inner frame 430 is prevented once the closed end of slots 669A, 669B contacts the wick 440, which coincides with the base section 436 of the inner frame being received into the lower portion 462 of the cartomizer plug 460. At this stage, the combination of cartomizer plug 460, heater/wick assembly 500, and inner frame 430, as shown in FIG. 6B has been formed, and the vent seal 420 can now be fitted onto the air tube (pipe) 432 of the inner frame 430.

Figure 7A:
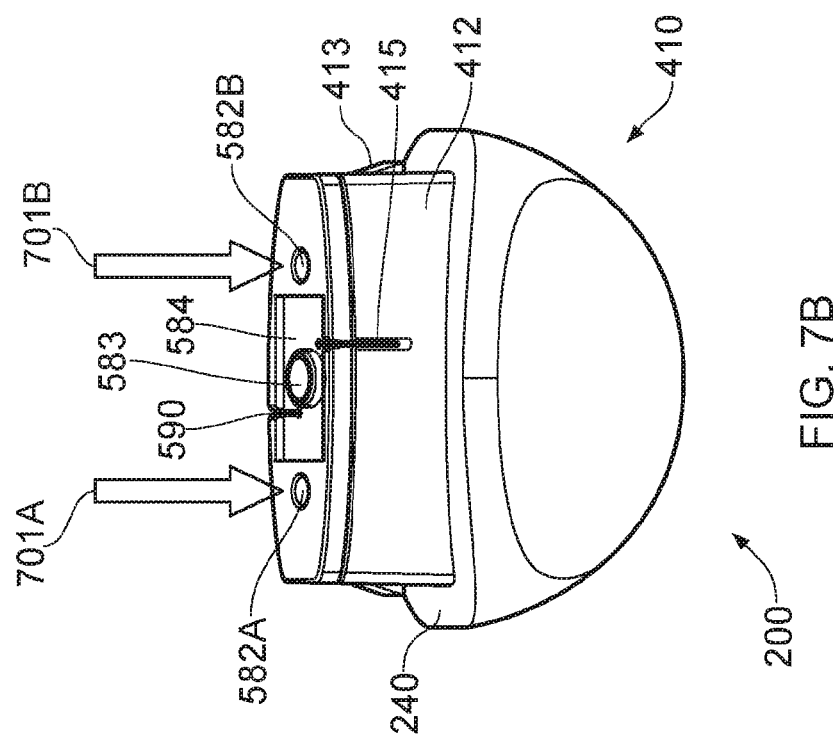
FIGS. 7A and 7B illustrate the combination of the inner frame, wick/heater assembly, and primary seal being fitted into the shell and the reservoir then being filled with e-liquid in accordance with some embodiments of the disclosure.
Figure 7B:
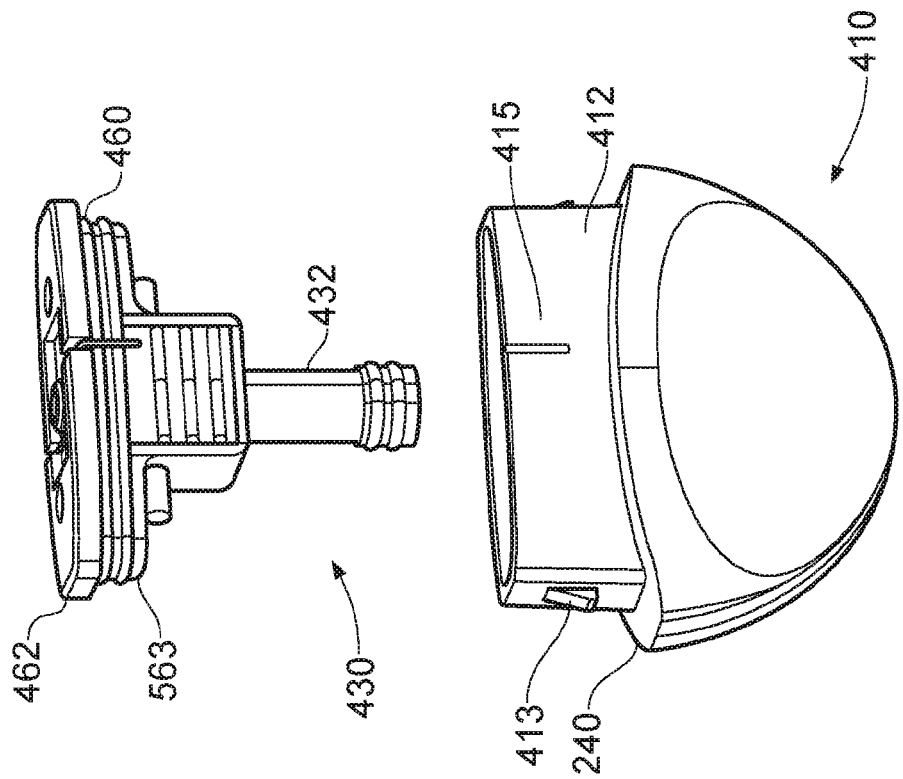

FIG. 7A illustrates the combination of the inner frame 430, wick/heater assembly 500, and primary seal 460 being fitted into the shell 410. As this insertion occurs, the slot 415 in each of the front and back faces of the lower portion 412 of the shell 410 accommodates a portion of wire 552 that has passed through slot 590 and has been wrapped back up around the outside of the cartomizer plug 460 and into groove 597. Furthermore, the deformable ribs 563 around the lower portion 462 of the primary seal are slightly compressed by the inside wall of the lower portion 412 of the shell 410 during the insertion, and thereby form a seal to retain the e-liquid in the resulting reservoir 270. Accordingly, as illustrated in FIG. 7B, the cartomizer 200 is now ready for filling with the e-liquid. This filling is performed, as indicated by arrows 701A, 701B, through holes 582A and 582B in the primary seal 460, and through slots 671A, 671B in the inner frame (not visible in FIG. 7B).

FIG. 8A illustrates the PCB 470 being fitted into the rectangular indentation 584 in the underside of the primary seal 460. This fitting aligns the central hole 471 in the PCB 470 with the central hole 583 in the primary seal 460 in order to provide the main airflow channel into the cartomizer 200.

As previously described, the rectangular indentation 584 is provided with a pair of holes 587, located on either side of the central hole 583. Each hole 587 allows egress of a respective contact wire 552A, 552B from the vaporizer chamber 465. The contact wires 552A, 552B are bent flat against the floor of the rectangular indentation 584, and then exit the rectangular indentation 584 via respective slots 590A, 590B in the front and back walls of the rectangular indentation 584. The final portion of each heater contact wire 552A, 552B, is then bent upwards, back towards the top of the cartomizer 200 and mouthpiece 250, and located in a corresponding groove or channel 597 formed in the cartomizer plug 460. In addition, the base portion of the shell also includes a slot 415 on each of the front and back faces to accommodate a respective heater contact wire 552A, 552B.

In accordance with some embodiments, the PCB 470 does not contain any active components, but rather provides two large contact pads 810A, 810B on either side of the central hole 471. These contact pads are visible in FIG. 8A on the lower face of the PCB 470, i.e. the side facing the control unit 300 after assembly. The opposite face of the PCB 470, i.e. the upper side which is received into the rectangular indentation 584 and faces the heater 450, is provided with a similar, corresponding configuration of contact pads (not visible in FIG. 8A). The heater contact wires 552A, 552B are in physical, and hence electrical, contact with a respective contact pad on the upper side of the PCB 470.

The opposing pairs of contact pads on either side of the PCB 470 are connected by respective sets of one or more vias 820A, 820B. In other words, vias 820A provide a conductive path between one contact pad on the lower face of the PCB 470 and a corresponding contact pad on the upper face of the PCB 470, and vias 820B provide a conductive path between the other contact pad on the lower face of the PCB 470 and its corresponding contact pad on the upper face of the PCB 470. Accordingly, when the control unit 300 is connected to the cartomizer 200, pins from the control unit 300 touch the contact pads on the lower side of the PCB 470, and electrical current flows to/from the heater 450 through the respective vias, contact pads on the upper side of the PCB 470, and respective heater contact wires 552A, 552B.

FIG. 8B illustrates the end cap 480 being fitted to the cartomizer 200 in accordance with some embodiments of the disclosure. In particular, the end cap 480 is fitted over the end of the cartomizer plug 460 and the lower section 412 of the shell 410, and is retained in this position by the protruding member 413 provided on each side of the lower section 412 of the shell engaging into the corresponding hole or slot 261 on each side of the end cap 480. In this fully assembled state (see FIG. 2), the end cap 480 covers and therefore closes the holes 582A, 582B in the cartomizer plug 460 that were used for filling the liquid reservoir 270. Indeed, as can be seen in FIG. 10A, the end cap 480 is provided with two upwardly directed plugs 870A and 870B that respectively penetrate and close the filling holes 582A, 582B. Accordingly, the reservoir 270 is now fully sealed, apart from the opening on each side of the atomizing chamber 465 through which the wick 440 passes into the atomizing chamber 465.

As previously discussed, the end cap 480 includes three holes, a central hole 214 and two holes 212A, 212B located on either side of this central hole 214. The fitting of the end cap 480 aligns the central hole 214 of the end cap 480 with the central hole 471 in the PCB 470 and with the central hole 583 in the primary seal 460 in order to provide the main airflow channel into the cartomizer 200. The two side holes 212A, 212B allow pins from the control unit 300, acting as positive and negative terminals, to pass through the end cap 480 and make contact with respective contact pads 810A, 810B on the lower side of the PCB 470, thereby enabling the battery 350 in the control unit 300 to supply power to the heater 450.

In accordance with some embodiments, the primary seal 460, which as noted above is made of a resilient deformable material such as silicone, is held in a compressed state between the inner frame 430 and the end cap 480. In other words, the end cap 480 is pushed onto the cartomizer 200 and compresses the primary seal 460 slightly before the latch components 413 and 261 engage with one another. Consequently, the primary seal 460 remains in this slightly compressed state after the end cap 480 and shell 410 are latched together. One advantage of this compression is that the end cap 480 acts to push the PCB 470 onto the heater contact wires 552A, 550B, thereby helping to ensure a good electrical connection without the use of solder.

FIG. 9 is a top view looking down onto the control unit 300 of the e-cigarette 100 of FIG. 1 in accordance with some embodiments of the disclosure. The control unit 300 includes external walls 315 that rise above the rest of the control unit 300 (as best seen in FIG. 1) to define a cavity for accommodating the lower portion 210 of the cartomizer 200. Each side of these walls 315 is provided with a spring clip 931A, 931B that engages with the hole or slot 260 on each side of the cartomizer 200 (see FIG. 2), thereby retaining the cartomizer 200 in engagement with the control unit 300 to form the assembled e-cigarette 100.

At the bottom of the cavity formed by the upper portion of control unit walls 315 (but otherwise at the top of the main body of the control unit 300) is a battery seal 910 (see also FIG. 1). The battery seal 910 is formed from a resilient (and compressible) material such as silicone. The battery seal 910 helps to mitigate one potential risk with an e-cigarette 100, which is that e-liquid leaks from the reservoir 270 into the main air passage through the device 100 (this risk is greater where there is free liquid in the reservoir 270, rather than the liquid being held by a foam or other such material). In particular, if e-liquid were able to leak into the portion of the control unit 300 containing the battery 350 and control electronics, then this might short circuit or corrode such components. Furthermore, there is also a risk that the e-liquid itself would then become contaminated before returning into the cartomizer 200 and then exiting through the mouthpiece hole 280. Accordingly, if any e-liquid does leak into the central air passage of the cartomizer 200, the battery seal 910 helps to prevent such leakage progressing into the portion of the control unit 300 that contains the battery 350 and control electronics. (The small holes 908 in the battery seal 910 do provide very limited fluid communication with the microphone 345 or other sensor device, but the microphone 345 itself can then act as a barrier against any such leakage progressing further into the control unit 300.)

As shown in FIG. 9, there is a small groove or spacing 921 around the perimeter between the top of the battery seal 910 and the inside of the walls 315 of the control unit 300; this is primarily formed by the rounded corner of the battery seal 910. The battery seal 910 is further provided with a central groove 922 from front to back, which connects at both ends (front and back) with the perimeter groove 921 to support airflow into the cartomizer 200, as described in more detail below. Immediately adjacent to central groove 922 are two holes 908A, 908B, one on either side of the groove 922. These air holes 908A, 908B extend down to the microphone 345. Thus when a user inhales, this causes a drop in pressure within the central air passage through the cartomizer 200, as defined by air tube 432, the central hole 583 in the primary seal 460, etc., and also within the central groove 922, which lies at the end of this central air passage. The drop in pressure further extends through holes 908A, 908B to the microphone 345, which detects the drop in pressure, and this detection is then used to trigger activation of the heater 450.

Also shown in FIG. 9 are two contact pins, 912A, 912B, which are linked to the positive and negative terminals of the battery 350. These contact pins 912A, 912B pass through respective holes in the battery seal 910 and extend through holes 212A, 212B of the end cap to make contact with contact pads 810A, 810B respectively on the PCB 470. Accordingly, this then provides an electrical circuit for supplying electrical power to the heater 450. The contact pins 912A, 912B may be resiliently mounted within the battery seal 910 (sometimes referred to as "pogo pins"), such that the mounting is under compression when the cartomizer 200 is latched to the control unit 300. This compression causes the mounting to press the contact pins 912A, 912B against the PCB contact pads 810A, 810B, thereby helping to ensure good electrical connectivity. It will be appreciated that approaches other than using pogo pins could be used. For example, in some cases the contact pins 912A, 912B may not be spring mounted, but may instead accommodate a degree of resilient deflection when assembled to facilitate a biased contract with the PCB contact pads. In another cases, the contact pins 912A, 912B may themselves be rigid and carried by a resiliently mounted support.

The battery seal 910, which as noted above is made of a resilient deformable material such as silicone, is held in a compressed state between the cartomizer 200 and the control unit 300. In other words, inserting the cartomizer 200 into the cavity formed by walls 315 causes the end cap 480 of the cartomizer 200 to compress the battery seal 910 slightly before the spring clips 931A, 931B of the control unit 300 engage with the corresponding holes 260A, 260B in the lower portion 210 of the cartomizer 200. Consequently, the battery seal 910 remains in this slightly compressed state after the cartomizer 200 and the control unit 300 are latched together, which helps to provide protection against any leakage of e-liquid, as discussed above.

FIGS. 10A and 10B are cross-sections respectively (a) from side to side, and (b) from front to back, showing the airflow through the e-cigarette 100 of FIG. 1 in accordance with some embodiments of the disclosure. The airflow is denoted in FIGS. 10A and 10B by the heavy black, dashed arrows. (Note that FIG. 10A only shows air flow on one side of the device 100, but there is an analogous air flow on the other side as well—having multiple such air inlets reduces the risk that a user will accidentally block the air inlets with their fingers while holding the device 100.)

The airflow enters through a gap at the sides of the e-cigarette 100, in between the top of the walls 315 of the control unit 300, and the flange or rim 240 of the cartomizer shell 410. The airflow then passes down a slight spacing between the inside of the walls 315 and the outside of the lower portion 210 of the cartomizer 200, past the spring clips 931, and hence into perimeter groove 921 (as shown in FIG. 9). The airflow is then drawn around the perimeter groove 921, and hence out of the plane of FIGS. 10A and 10B (so that this portion of the airflow path is therefore not visible in these two diagrams). Note that there is typically some space above the groove 921 between the inside of the control unit walls 315 and the outside of the cartomizer end cap 480, so the airflow is not necessarily constrained to the groove 921 per se.

After travelling an angle of approximately 90 degrees around the perimeter groove 921, the airflow passes into the central groove 922, from where it travels to and through the central hole 583 of the end cap 480 and hence into the central air passage of the cartomizer 200. Note that FIG. 10B shows this airflow along the central groove 922 into the central air passage, and then the flow of air up through the central air passage is shown in both FIGS. 10A and 10B. In contrast to groove 921, the space above groove 922 is not open, but rather the battery seal 910 is compressed against the end cap 480 of the cartomizer 200. This configuration results in the end cap 480 covering the groove to form a closed channel having a confined space. This confined channel can be utilized to help control the draw resistance of the e-cigarette 100, as described in more detail below.

There are various benefits associated with the overall airflow path such as shown in FIGS. 10A and 10B. The airflow detector, such as microphone 345, is generally located in the control unit 300. This reduces cost because the microphone is therefore in the reusable portion of the device, and so there is no need to include a microphone in every cartomizer (the disposable component). In addition, having the microphone 345 in the control unit 300 allows the microphone to be readily connected to the battery 350 and to the control processor of the control unit 300 (not shown in the Figures).

On the other hand, it is generally desirable to reduce or avoid an airflow past electronics components, for example, because such electronics components tend to become warm with use, and may potentially shed volatiles. It will be appreciated that the airflow path shown in FIGS. 10A and 10B largely bypasses the electronic components of the control unit 300, with only the small holes 908 branching off this main airflow to allow the microphone 345 to detect a change in pressure. This avoidance of airflow past the main electronic components of the control unit 300 has been achieved despite the fact that the cartomizer 200 sits quite deeply within the control unit 300 (which helps to reduce the overall length of the device 100).

Furthermore, in many existing e-cigarettes, the overall air path is not tightly controlled. For example, air may leak into the air path at joins between various components (such as between the cartomizer 200 and control unit 300), rather than just at the dedicated air inlet(s). This leakage (as well as various other manufacturing variations) may result in significant variation in the draw resistance of the device, where the draw resistance in effect represents the pressure difference needed to produce a given air flow through the device 100. This variation in draw resistance can prevent a consistent user experience and can also effect the operation of the device 100. For example, if the draw resistance is high, it is likely that the flow of air through the device 100 may be reduced, which in turn reduces the amount of air cooling experienced by the heater 450.

Accordingly, the approach described herein provides an e-cigarette device including: an atomizer for vaporizing a liquid; an air passage through the atomizer, the air passage exiting the e-cigarette at a mouthpiece; at least one air inlet joined by a channel to the air passage through the vaporizer; and at least one resilient seal which acts to prevent air from the air inlet travelling to the air passage except through the channel.

For example, in the implementation described above, the air flow entering the central air passage through the vaporizer must first travel along groove 922. This groove, in conjunction with the bottom of the end cap 480 that in effect provides a top surface or closure for the groove, defines the airflow channel through the control unit 300 into the cartomizer 200.

In such a device, air from the air inlet must necessarily travel through the channel to reach the air passage (because the seal prevents other routes). Accordingly, the channel provides a point of control for the draw resistance—especially if the channel provides the majority of the draw resistance for the air path through the whole device. In particular, as long as the draw resistance for the channel (which is determined largely by the size of the channel) is reasonably constant between devices (and between different usages of the same device), then the draw resistance for the device as a whole will likewise be reasonably constant.

In some implementations, the e-cigarette may further comprise a facility to alter the predetermined draw resistance for the e-cigarette. This facility may allow a user to set the predetermined draw resistance for the e-cigarette to one of a limited number of discrete values according to individual preference, etc. For example, for the e-cigarette described herein, there may be two successive latch positions between the cartomizer 200 and the control unit 300, which result in a lower or greater compression of the battery seal 910. The lower compression will generally allow groove 922 to expand slightly, and hence provide a lower draw resistance than the latch position which produces the higher compression of the battery seal 910. Another way of implementing this facility would be to provide some baffle that can be moved into the channel or groove 922 to partly obstruct the airflow by a desired amount.

The seal may be formed of a resilient material, such as silicone, and the channel is formed at least in part by the seal material itself. For example, in some embodiments, the channel is defined by a resilient material compressed against a surface of a rigid material, such as the battery seal 910 pressing against the end cap 480, and the surface of the rigid material may include a hole, such as hole 583 in end cap 480, that connects from the channel 922 into the air passage through the atomizer. Note that the channel may in fact comprises a network of multiple (sub) channels as appropriate, according to the particular implementation.

As described above, the device may include a cartomizer 200 and a control unit 300, and the resilient seal is provided as part of the control unit 300 that contacts the exterior of the cartomizer 200 when the cartomizer 200 is joined to the control unit 300. The resilient material may be held under compression between the cartomizer 200 and the control unit when the cartomizer 200 is joined to the control unit 300, such as by a latch mechanism. This compression of the resilient material helps to provide an air-tight seal around the edges of the seal.

A further consideration is that for some e-cigarettes, there is a risk that the e-liquid may leak 270 into main air passage. In such a situation, the seal helps to ensure that the e-liquid is only able to travel from the air passage into the air channel, thereby helping to prevent the e-liquid coming into contact with the battery and other electrical components. Furthermore, the air channel may be sufficiently narrow to prevent significant flow of e-liquid through the channel, which further helps to constrain any leaked e-liquid.

Figure 11A:
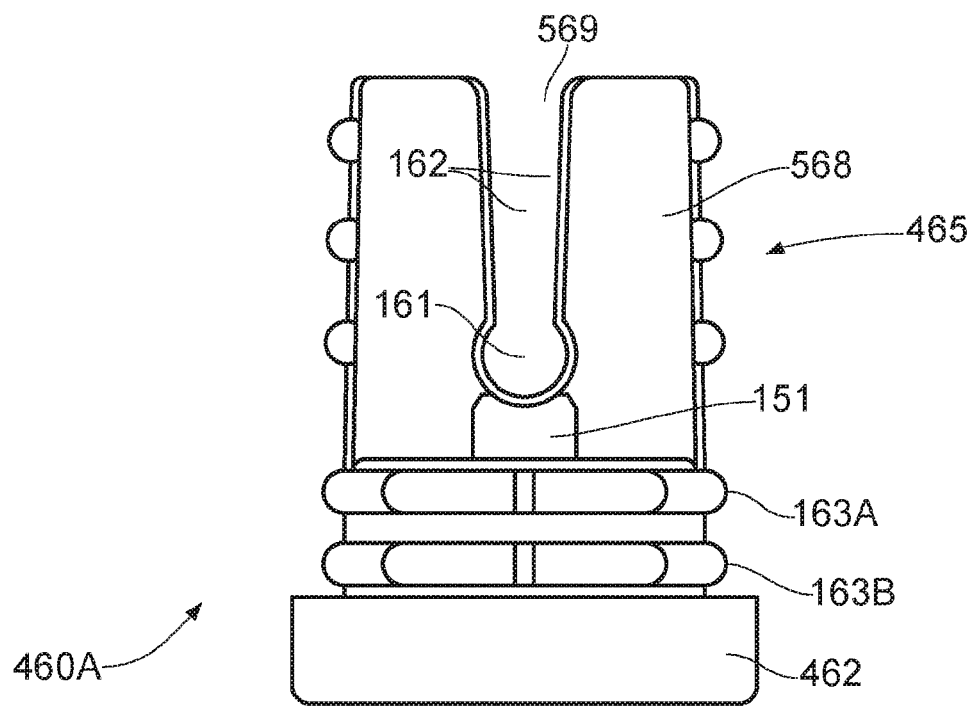
FIGS. 11A and 11B are a side view and a perspective view, respectively, of the cartomizer plug in accordance with some embodiments of the disclosure.
Figure 11B:
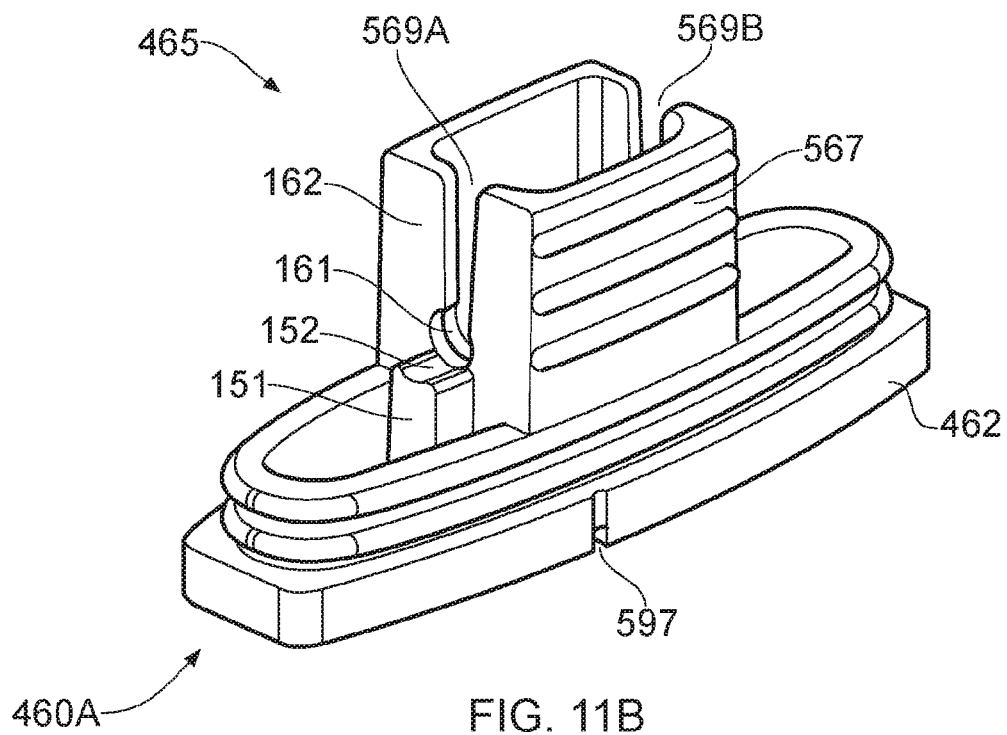
Figure 12:
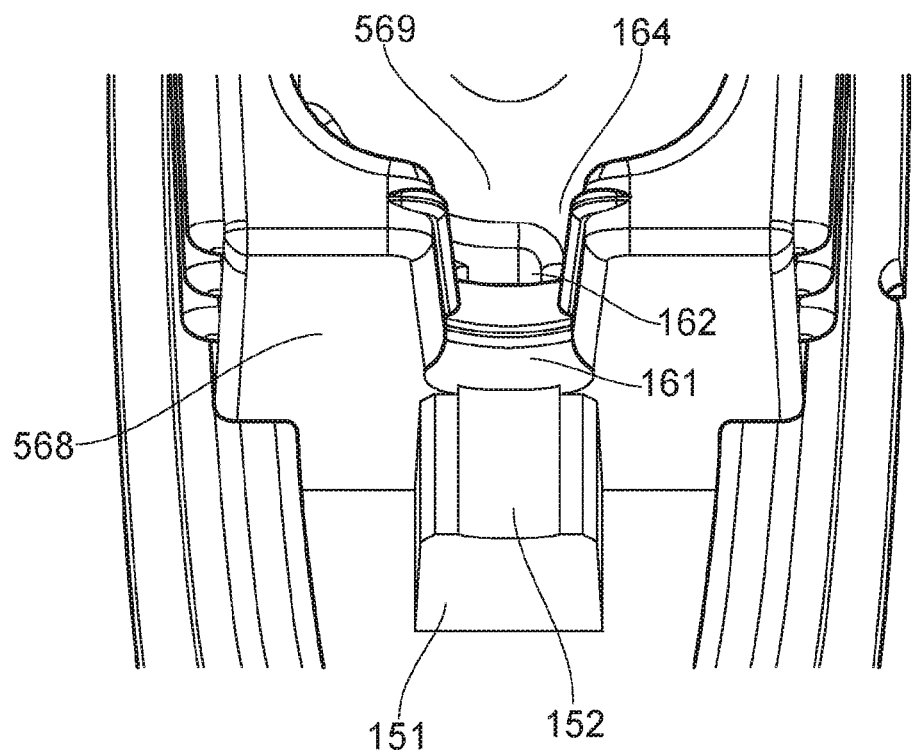
FIG. 12 is a detailed view of a portion of the cartomizer plug of FIGS. 11A and 11B in accordance with some embodiments of the disclosure.
Figure 13:
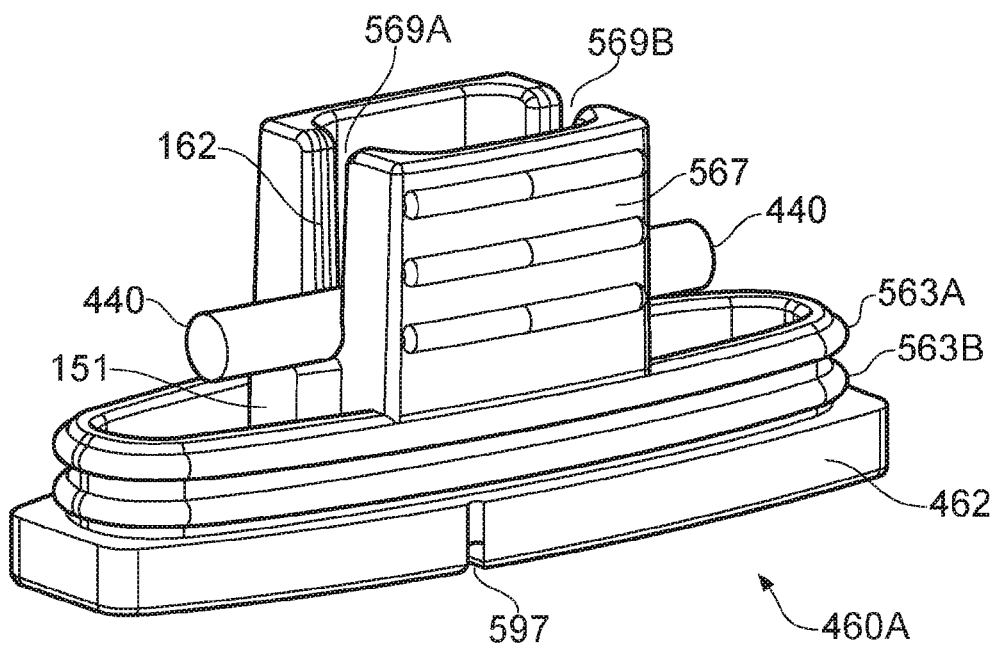
FIG. 13 is a perspective view of the cartomizer plug of FIGS. 11A and 11B assembled with a wick in accordance with some embodiments of the disclosure.

FIGS. 11A and 11B are a side view and a perspective view respectively of another implementation of the cartomizer plug or primary seal in accordance with some embodiments of the disclosure. The cartomizer plug 460A shown in these Figures can be used, if so desired, as a replacement for the cartomizer plug 460 previously described. The cartomizer plug 460A is further illustrated in FIG. 12, which provides a detailed view of a portion of the cartomizer plug 460A of FIGS. 11A and 11B in accordance with some embodiments of the disclosure, and also in FIG. 13, which is a perspective view of the cartomizer plug 460A of FIGS. 11A and 11B assembled with a wick in accordance with some embodiments of the disclosure.

Cartomizer plug 460A shares many features with the cartomizer plug 460 previously described, including: a base portion 462 with ribs 563A, 563B and grooves 597 for the upturned heater contact wires; and an atomizing chamber 465 with front and back walls 567, side walls 568, and slots 569A, 569B for receiving wick 440. The cartomizer plug 460A differs from cartomizer plug 460 in three main aspects.

Firstly, the shape of the slots 569 has been modified slightly, in that the slots no longer have parallel sides or edges descending to a U-shaped closed end, such as shown in FIG. 4. Rather, each slot now comprises two portions, a stem portion 162 that leads downwards from the open end of the slot to a wick retaining portion 161 located at the closed end of the slot. The sides or edges of the stem portion 162 are no longer parallel, but rather open out towards to the top of the slot 569, i.e. towards the open end of the slot. It will be appreciated that this opening out of portion stem 162 helps to allow the wick 440 to be inserted into the slot 569 more easily. Conversely, the sides or edges of the stem portion 162 approach one another in the depth direction towards the closed end of the slot 569. Typically therefore, the wick 440 will be slightly compressed by this narrowing stem 162 (in a direction perpendicular to the main longitudinal axis of the wick) as the wick 440 is inserted down the slot 569.

At the closed end of the slot 569 is the wick retaining portion 161, which forms a curved aperture. The curvature of the wick retaining portion 161 slightly exceeds a total of 180 degrees, hence the slot 569 has in effect a narrowed region or neck where the wick retaining portion 161 joins the stem portion 162. It will be appreciated that this configuration of the slot 569, including the wick retaining portion 161 with the neck of reduced thickness, helps to maintain the wick 440 in the correct position at the closed, bottom end of the slot 569, since the wick 440 would generally have to be compressed again in order to pass back upwards through the neck above the wick retaining portion 161.

A second difference between the cartomizer plug 460A and the cartomizer plug 460 is that for the former, the inner walls or edges of the slot 569 are provided with a lip seal 164. In particular, this lip seal 164 comprises a slight ridge that protrudes from the inner walls of the slot 569, and hence is directed inwardly with respect to the slot 569 itself. The ridge runs down both sides of the stem portion 162 of the slot 569, and also runs around the curved inner surface of the wick retaining portion 161.

The lip seal is made of a resilient material, such as silicone, and when the wick 440 is inserted into the slot 569, the lip seal 164 is compressed and/or deflected sideways (in effect, bent over) in order to accommodate the wick. In this compressed or deflected state, the lip seal is therefore biased against the wick 440. This helps to provide a more effective seal between the reservoir 270 and the atomizing chamber 465, in that there is no space between the lip seal 164 and the wick 440 for liquid to flow directly from the reservoir 270 into the atomizing chamber 465. Rather, any transfer of e-liquid from the reservoir 270 into the atomizing chamber 465 must occur in a controlled manner via the wick 440, whereby the material of the wick 440 itself constrains such flow. In particular, the wick 440 holds the liquid in the atomizing chamber 465 until this liquid is vaporized by the heater 450, in which case the wick 440 will draw replacement e-liquid into the atomizing chamber 465 from reservoir 270. Such a configuration therefore helps to reduce the risk of free liquid being leaked into the main airflow passage of the e-cigarette 100.

Note that the wick 440 itself is compressible to some extent, since it is formed of multiple glass fibers (or other fibrous material). If a very tight seal were to be formed around the wick 440, such that the wick 440 and fibers are tightly compressed, such a tight seal might well be effective as a seal, but it would also degrade the performance of the wick 440, making it much harder for the wick 440 to transport e-liquid from the reservoir 270 into the atomizing chamber 465. The resilience of the lip seal 164 is therefore arranged to ensure that the bias force resulting from the compression or deflection of the lip seal has comparatively little effect on the wick 440, and so does not impact the performance of the latter as regards transporting liquid into the atomizing chamber for vaporization. For example, if the lip seal is relatively thin, then it can be deflected by the wick 440 with relatively little reaction force being created back onto the wick 440.

Although the lip seal of cartomizer 460A is formed from a single ridge, it will be appreciated that in some implementations multiple ridges may be utilized instead. Furthermore a lip seal could also be provided if so desired in the corresponding slots 669A, 669B of the inner frame and/or on pedestal 151 (instead of or in additional to the lip seal 164 in slots 569).

A third difference between the cartomizer plug 460A and the cartomizer plug 460 is that for the former, a pedestal 151 is provided adjacent each side wall 568, outside the atomizing chamber. When the wick 440 is inserted into the slots 569, and in particular, with the wick 440 located in the wick retaining portion 161 of the slots 569, the wick 440 rests on surface 152 located at the top of each pedestal 151. Supporting the wick 440 in this manner at each end by the pedestals 151 helps to avoid distortion of the wick 440, either caused by the weight of the end regions of the wick 440 itself, and/or by the inner frame 430 pressing down on the wick 440, for example as part of the assembly step shown in FIGS. 6A and 6B. The prevention of such distortion of the wick 440 generally helps to maintain an appropriate and consistent flow of e-liquid into the atomizing chamber, and also helps to reduce the risk of liquid leakage that might otherwise occur from such distortion of the wick 440.

Although various embodiments have been described in detail herein, this is by way of example only, it will be appreciated that a channel to constrain airflow into a device 100 may be utilized in many different configurations. For example, this approach might be used for a one-piece or three-piece device (rather than a two-piece device, i.e. cartomizer 200 and control unit 300, as described here). Similarly, this approach could be utilized with electronic vapor provision systems that includes material derived from tobacco plants which is provided in any suitable form (powder, paste, shredded leaf material, etc, i.e. not liquid), and then heated to produce volatiles for inhalation by a user. This approach could also be used with various types of heater for the e-cigarette, various types of airflow configuration, various types of connection between the cartomizer and the control unit (such as screw or bayonet) etc. The skilled person will be aware of various other forms of electronic vapor provision system which might utilize a channel for restricting the airflow as described herein.

Furthermore, it will be appreciated the manner of cartomizer assembly set out above is merely one example, and an assembly process comprising different steps, or a similar steps performed in a different order may also be adopted. For example, with reference to the steps set out in relation to FIGS. 6B, 7A and 7B, in another example instead of fitting the vent seal 420 to the air tube (pipe) 432 of the inner frame (FIG. 6B) before placing the combined assembly in the shell 410 (FIGS. 7A and 7B), the vent seal 420 might first be mounted in position in the shell 410 so that it mounts to the air tube (pipe) 432 of the inner frame when the inner frame 430, wick/heater assembly 500, and primary seal 460 are together fitted into the shell 410. Similarly, with reference to the steps set out in relation to FIGS. 8A and 8B, in another example instead of placing the PCB 470 in its indentation 584 in the cartomizer plug 460 before attaching the cap 480 to complete the cartomizer assembly, the PCB 470 might first be mounted in position in the cap 480, and then the cap 480, with PCB 470 attached, connected to the shell 410. The PCB 470 may mount to the cap 480 by a friction/press fit, for example. The cap 480 may include locating pegs, or other guide mechanism, to help position the PCB 470 in the cap 480 so it is aligned with the indentation 584 in the cartomizer plug 460 when the cap 480 is attached to the shell 410.

Figure 14:
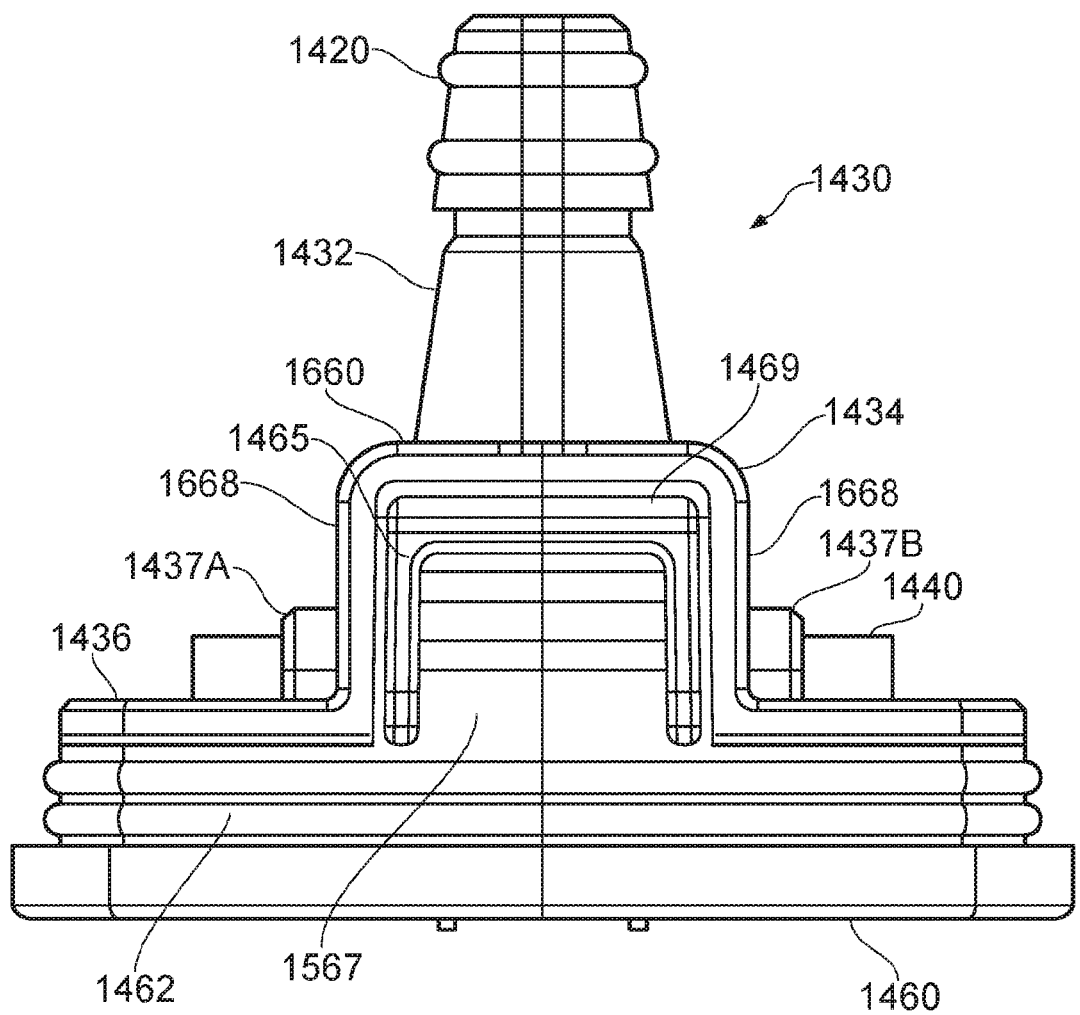
FIG. 14 is a front view of the cartomizer plug, inner frame, vent seal and wick in accordance with some other embodiments of the disclosure.

FIG. 14 onwards (through to FIG. 19) illustrate a further variation on certain aspects of the cartomizer 200 described above. The implementation of FIG. 14 onwards generally comprises the same components as the implementation shown in FIG. 4 (for example), but there are some slightly changes to the individual components. For ease of reference, components in FIG. 14 onwards are given the same reference number as in the previous Figures, but preceded by a "1", so that (for example) the vent seal of FIG. 4 has reference numeral 420, while the vent seal of FIG. 14 has reference numeral 1420. Note that corresponding components, such as the vent seal 420 and the vent seal 1420, generally have the same structure, material, functionality, etc., as each other unless otherwise indicated. Furthermore, it will be appreciated that some implementations may adopt certain components or features from FIGS. 1-13 in combination with certain components or features from FIG. 14 onwards (having regard as appropriate to any inter-dependencies between the various components and features).

FIG. 14 shows a side view of the internal cartomizer components (analogous to FIG. 6B after the vent seal has been assembled onto the inner frame). In particular, FIG. 14 shows a vent seal 1420 located on top of an airflow tube 1432 of the inner frame 1430. The inner frame 1430 further comprises a middle section 1434, which surrounds part of the atomizing chamber, and a base portion 1436. The middle section 1434 includes opposing side walls 1668, plus top wall 1660 (at the bottom of airflow tube 1432); together side walls 1668 and top wall 1660 define in part the atomizing chamber. A wick 1440 is inserted into the inner frame (from underneath), and passes through the atomizing chamber. The cartomizer plug 1460 is also inserted into the inner frame 1430 (again from underneath) to hold the wick 1440 in position. The cartomizer plug 1460 comprises an upper section 1465 which completes the atomizing chamber (in conjunction with the inner frame 1430), and a lower portion 1462 that provides an end seal for the liquid reservoir 270. Note that the inner frame 1430 and the cartomizer plug 1460 are provided with slots (not visible in FIG. 14, but analogous to those shown in FIG. 6) for receiving and retaining the wick 1440 in the atomizing chamber.

Figure 15:
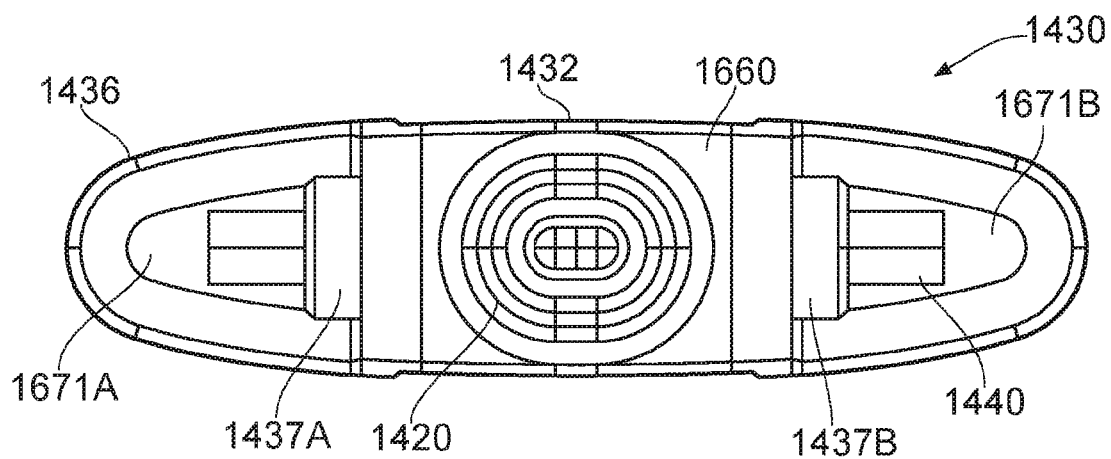
FIG. 15 is a top view looking down onto the inner frame, wick and vent seal of FIG. 14 in accordance with some embodiments of the disclosure.

FIG. 15 shows a top view of the vent seal 1420, inner frame 1430 and wick 1440 (but without the cartomizer plug 1460). In addition to the features mentioned above in respect of FIG. 14, FIG. 15 also shows openings 1671A and 1671B on either side of the lower portion 1436 of the inner frame 1430. These openings allow the wick 1440 to pass through the lower portion 1436 of the inner frame during assembly. Also visible in FIG. 15 (and FIG. 14) are two arches 1437A and 1437B, which are formed integrally with the inner frame 1430 and extend outwards from the side walls 1668 of the inner frame 1430. These arches 1437A, 1437B are positioned at the end of the slots for receiving the wick 1440, such that they can be considered as a lateral extension (in the X-dimension) of the roof of these slots. In other words, the inside of each arch forms a continuous surface with the roof of the adjacent slot, shaped to match and accommodate the cylindrical surface of the wick 1440 as received into the slots. The addition of arches 1437A,B helps to retain the wick 1440 in the correct location in the atomizing chamber, and also helps to reduce liquid leakage from the reservoir 270 surrounding the inner frame into the atomizing chamber (i.e. so that the only flow from reservoir 270 into the atomizing chamber is along wick 1440 itself).

Figure 16A:
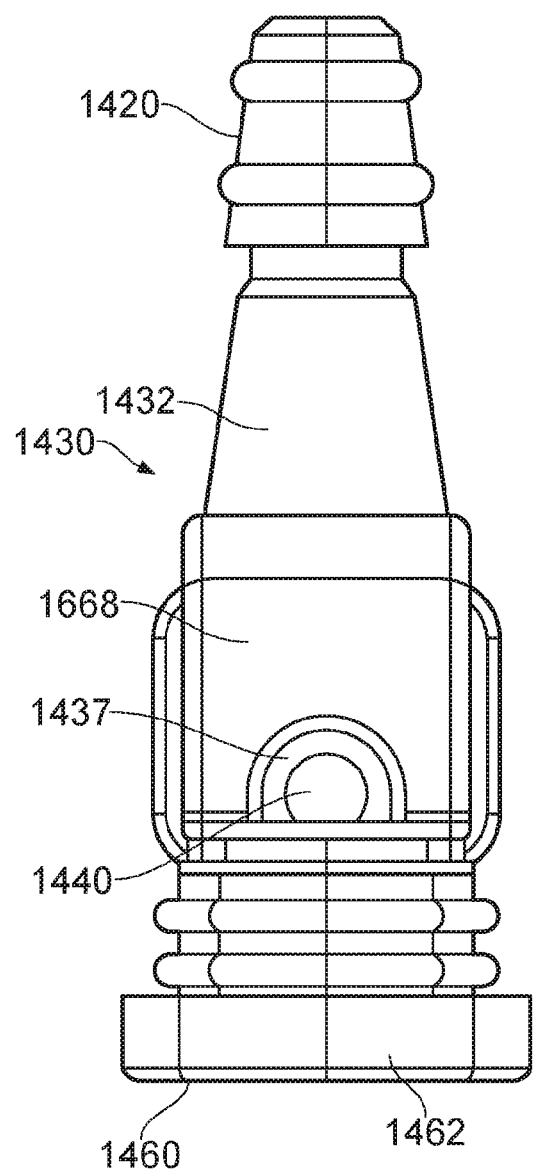
FIG. 16A is a side view of the cartomizer plug, inner frame, vent seal and wick of FIG. 14 in accordance with some embodiments of the disclosure.
Figure 16B:
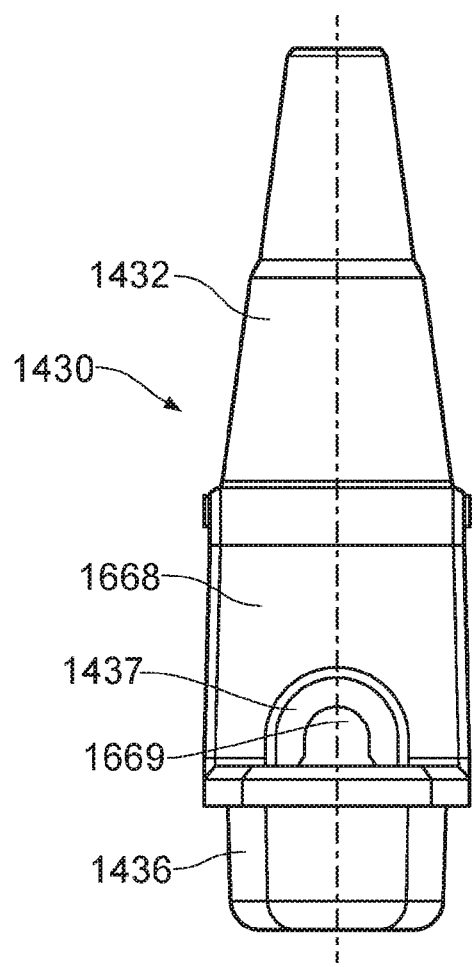
FIG. 16B is a corresponding side view to FIG. 16A, but just of the inner frame (i.e. omitting the vent seal, wick, and cartomizer plug).

FIGS. 16A and 16B present side views of the inner frame 1430. More particularly, FIG. 16A shows the inner frame 1430 in combination with the vent seal 1420, wick 1440 and cartomizer plug 1460, whereas FIG. 16B shows just the inner frame 1430. It can be seen from FIGS. 16A and 16B that the arch 1437 extending from side wall 1668 is generally in the shape of an upside-down "U", where the curved portion of the arch is semi-circular in shape for receiving the circular wick 1440, and the two short straight walls of each arch descend downwards (away from the mouthpiece end). The inner surface of the arch 1437 is generally aligned (and continuous) with the roof of adjacent slot 1669 formed in side wall 1668. As shown in FIG. 16B, these two short straight walls of the arch taper slightly outwards from one another at the bottom (furthest from the curved roof of the arch), and thereby act as a guide to help receive the wick 1440 into the arch 1437. Furthermore, the walls of the arch 1437 may also extend to, and contact, pedestal 151 of the cartomizer plug 1460 (see FIG. 11). In effect therefore, the wick 1440 is surrounded by arch 1437 in combination with pedestal 151, and as noted above, this configuration can help to reduce leakage and retain the wick 1440 in position (e.g. by resisting rotation of the wick 1440 about its main longitudinal axis and/or or displacement of the wick 1440 parallel to its main axis).

Returning to FIG. 14, the front wall 1567 (and analogous back wall—not visible in FIG. 14) of cartomizer plug 1460 is slightly different from front wall 567 of cartomizer plug 460, such as shown in FIG. 4. In particular, front wall 567 of cartomizer plug 460 comprises three horizontal ribs or ridges. In contrast, the front wall 1567 of cartomizer plug 1460 comprises two horizontal ribs or ridges, plus two vertical ribs on either side of the front wall 1567. Moreover, the two vertical ribs are joined by a cross ridge (also termed a bump ridge) 1469 at the top of the front wall 1567. There is a similar structure on the back wall of the cartomizer plug 1460 (not visible in FIG. 14).

Figure 17:
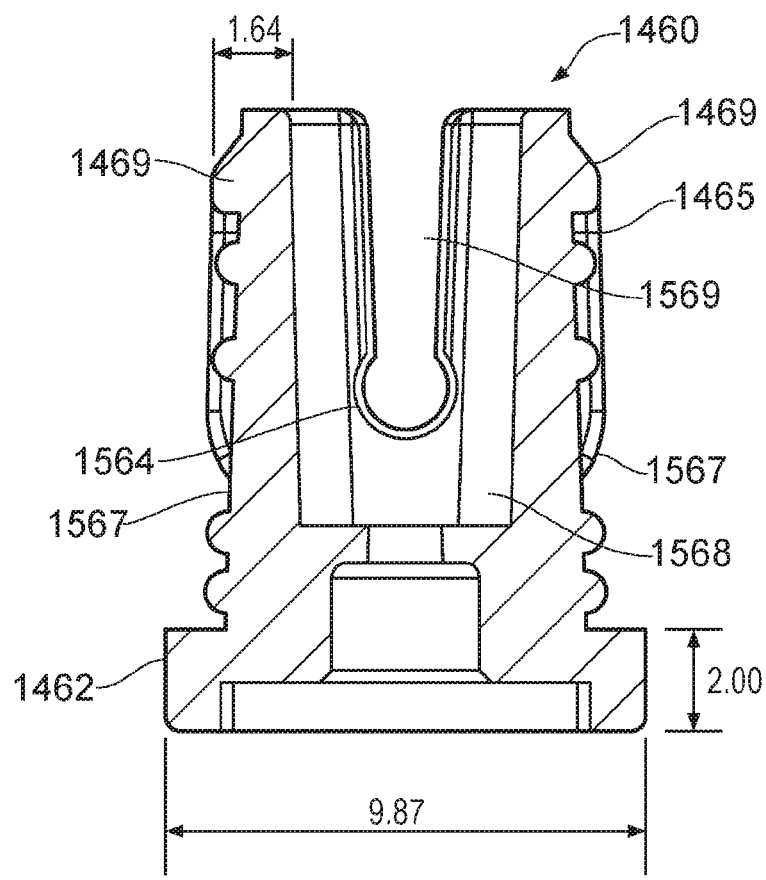
FIG. 17 is a cross-section through the centre of the cartomizer plug of FIG. 14 in accordance with some embodiments of the disclosure, in a plane perpendicular to the wick.

FIG. 17 is a cross-section through the cartomizer plug 1460 (by itself) in a plane normal to the main longitudinal axis of the wick (i.e. the Y-Z plane of FIG. 1), passing through the center of the atomizing chamber. This Figure includes dimensions of the cartomizer 1200 (in millimeters), but these are given only by way of example, and may vary from one implementation to another. A cartomizer slot 1569 for receiving wick 1440 is formed in a side wall 1568 of the atomizing chamber. The wick 1440 is received into this slot 1569 and sits at the end 1564 of the slot 1569. Note that slot 1569 is generally similar to slot 569 (such as described in relation to FIG. 11).

Also visible in FIG. 17 is the bump ridge 1469, located along the top of each side wall 1567. The bump ridge 1469 helps to give additional strength and stability to this top portion of the cartomizer plug 1460 when assembled with the inner frame 1430. For example, the bump ridge 1469 can help to improve the seal between the top of the cartomizer plug 1460 and the inner frame 1430 to further reduce leakage from the liquid reservoir 270 into the atomizing chamber.

Figure 18:
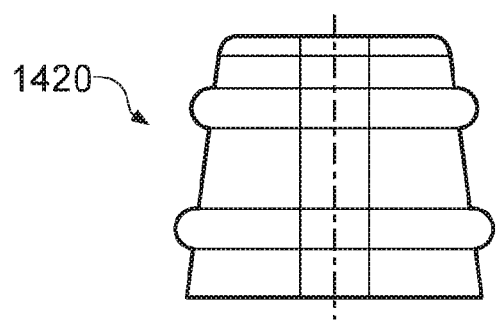
FIG. 18 comprises a front view (left) and a side view (right) of the vent seal of FIG. 14 in accordance with some embodiments of the disclosure.

FIG. 18 shows two views of the vent seal 1420 by itself, the drawing to the left is a front (or back) view, while the drawing to the right is a side view. Compared with the vent seal 420 shown in FIG. 4 (for example), it can be seen that vent seal 1420 is slightly longer (in the main axial direction of the device, i.e. parallel to the Y axis). In addition, the cross-section of the vent seal 1420 is oval in shape (rather than circular) and the vent seal tapers inwards towards the mouthpiece. This oval shape is also apparent from the top view of FIG. 15.

FIGS. 14 and 16 show that the airflow tube 1432 of the inner frame 1430 has a corresponding shape to the vent seal 1420, in that it is again oval in cross-section (in the X-Z plane, perpendicular to the main airflow direction), and tapers towards the mouthpiece 250 of the device 100. It will be appreciated that this correspondence in shape between the vent 1420 and the inner frame 1430 allows the vent seal 1420 to fit onto the inner frame 1430. Note also that the airflow tube 1432 of the inner frame 1430 shown in FIGS. 14 and 16 is slightly shorter than the airflow tube 432 of the inner frame 430 shown in FIG. 4. This reduced height of the airflow tube 1432 (compared with airflow tube 432) compensates for the increased height of the vent seal 1420 (compared with vent seal 420), such that the overall height of the cartomizer 200 is substantially unchanged.

Figure 19:
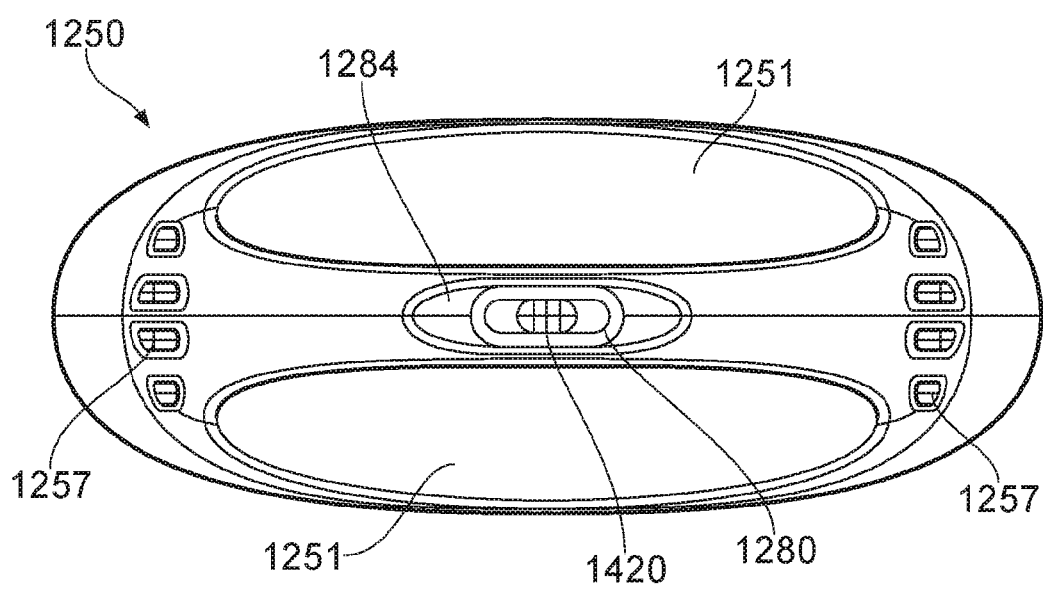
FIG. 19 is a top view of the mouthpiece for use with the cartomizer plug, inner frame, vent seal and wick of FIG. 14 (or of FIG. 4) in accordance with some other embodiments of the disclosure.

FIG. 19 is a top view of the mouthpiece 1250, which comprises two primary curved faces 1251 (analogous to curved faces 251 of mouthpiece 250 shown in FIG. 3). The mouthpiece 1250 differs from mouthpiece 250 in having slight indentations or holes 1257 on either side of the mouthpiece. These indentations represent a form of texturing, and can be used to hold the mouthpiece 1250 more easily, as well as reducing the thickness of the mouthpiece 1250 in this region (which can assist with molding). In addition, the mouthpiece 1250 includes an airflow exit hole 1280 within a valley region 1284. However, compared to the hole 280 in valley region 284 of mouthpiece 250, which is circular, hole 1280 is elongated in the width direction (X-axis) of the mouthpiece 1250, and hence has an oval or elliptical shape. This increase in size of the mouthpiece hole 1280 allows the vent seal 1420 to be visible through the mouthpiece hole 1280.

In conclusion, in order to address various issues and advance the art, this disclosure shows by way of illustration various embodiments in which the claimed invention(s) may be practiced. The advantages and features of the disclosure are of a representative sample of embodiments only, and are not exhaustive and/or exclusive. They are presented only to assist in understanding and to teach the claimed invention(s). It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope of the claims. Various embodiments may suitably comprise, consist of, or consist essentially of, various combinations of the disclosed elements, components, features, parts, steps, means, etc other than those specifically described herein. The disclosure may include other inventions not presently claimed, but which may be claimed in future.

The invention claimed is:

1. A cartomizer for a vapor provision system, the cartomizer comprising:
   a container for holding a reservoir of free liquid to be vaporized;
   an atomizing chamber;
   a porous wick extending from inside the container, through an aperture in a wall of the atomizing chamber, to inside the atomizing chamber in order to convey the liquid from the reservoir to the inside of the atomizing chamber for vaporization; and
   a resilient seal provided in the aperture to restrict the liquid from entering the atomizing chamber from the reservoir except by travelling along the wick;
   wherein the resilient seal is provided as a lip seal comprising a resilient ridge formed on the inside of the aperture and protruding at least partly into the aperture, wherein the lip seal is at least one of compressed or and/or deflected when the wick is located in the aperture.

2. The cartomizer of claim 1, wherein the resilience of the resilient seal is such as to restrict liquid from entering the atomizing chamber around the wick without significantly impacting the ability of the wick itself to transfer liquid from the reservoir into the atomizing chamber.

3. The cartomizer of claim 1, wherein the resilient seal is made of a resilient material.

4. The cartomizer of claim 3, wherein the resilient seal is made of silicone.

5. The cartomizer of claim 1,
   wherein the atomizing chamber includes first and second opposing side walls, the atomizing chamber being formed between the first and second opposing side walls, and the container for holding free liquid being provided outside the first and second opposing side walls,
   wherein the wick extends through a first aperture in the first side wall and a second aperture in the second side wall,
   and wherein a first resilient seal is provided in the first aperture and a second resilient seal is provided in the second aperture to restrict the liquid from entering the atomizing chamber from the reservoir except by travelling along the wick.

6. A cartomizer for a vapor provision system, the cartomizer comprising:
   a container for holding a reservoir of free liquid to be vaporized;
   an atomizing chamber;
   a porous wick extending from inside the container, through an aperture in a wall of the atomizing chamber, to inside the atomizing chamber in order to convey the liquid from the reservoir to the inside of the atomizing chamber for vaporization; and
   a resilient seal provided in the aperture to restrict the liquid from entering the atomizing chamber from the reservoir except by travelling along the wick;
   wherein the atomizing chamber includes first and second opposing side walls, the atomizing chamber being formed between the first and second opposing side walls, and the container for holding free liquid being provided outside the first and second opposing side walls,
   wherein the wick extends through a first aperture in the first side wall and a second aperture in the second side wall,
   and wherein a first resilient seal is provided in the first aperture and a second resilient seal is provided in the second aperture to restrict the liquid from entering the atomizing chamber from the reservoir except by travelling along the wick.

7. The cartomizer of claim 6, wherein the first and second side walls have respective first and second slots therein, each of the first and second slots having an open end and a closed end, and wherein the first and second apertures are located at the closed ends of the first and second slots, respectively.

8. The cartomizer of claim 6, wherein each of the first and second slots has a stem portion extending from an open end of the first or second slot to the closed end, and wherein a neck is formed between the stem portion and the aperture located at the closed end, a width of the neck being less than a width of the aperture.

9. The cartomizer of claim 8, wherein there is a gradual decrease in the width of the first or second slot between the open end and the neck.

10. The cartomizer of claim 6, further comprising third and fourth opposing side walls configured to overlap, respectively, with the first and second opposing side walls, the third and fourth opposing side walls being provided with third and fourth slots, respectively, each of the third and fourth slots having an open end and a closed end, wherein the closed ends of the third and fourth slots further define the first and second apertures, respectively.

11. The cartomizer of claim 10, further comprising first and second pedestals located, respectively, in the third and fourth slots, wherein the first and second pedestals support the wick in the first and second apertures, respectively.

12. The cartomizer of claim 10, wherein each of the closed ends of the first, second, third and fourth slots is provided with a resilient seal to restrict the liquid from entering the atomizing chamber from the reservoir except by travelling along the wick.

13. The cartomizer of claim 10, wherein each of the third and fourth opposing side walls is provided with an arch extending away from the atomizing chamber, each arch being sized to match and accommodate the wick.

14. The cartomizer of claim 10, further comprising first and second pedestals located, respectively, in the third and fourth slots, wherein the first and second pedestals support the wick in the first and second apertures, respectively, wherein each of the third and fourth opposing side walls is provided with an arch extending away from the atomizing chamber, each arch being sized to match and accommodate the wick, and wherein the curved portion of each arch contacts the wick opposite to a respective pedestal.

15. The cartomizer of claim 14, wherein the curved portion of each arch represents a continuation of the closed end of a respective one of the third and fourth slots.

16. The cartomizer of claim 1, wherein the wick is made from a fibrous material.

17. The cartomizer of claim 16, wherein the wick is made from glass fiber rope.

18. The cartomizer of claim 1, wherein the wick is made from a ceramic.

19. The cartomizer of claim 1, wherein the wick supports a heater coil inside the atomizing chamber.

20. The cartomizer of claim 1, wherein the reservoir is formed between an outer housing of the cartomizer and the atomizing chamber.

21. The cartomizer of claim 1, wherein the cartomizer is configured as a disposable component to be used with a reusable control unit of a vapor provision system.

22. A vapor provision system comprising the cartomizer of claim 1.

23. The vapor provision system of claim 22, wherein the cartomizer is formed as an integral part of the vapor provision system.

24. The vapor provision system of claim 22, wherein the cartomizer is a disposable component of the vapor provision system to be used with a reusable control unit of the vapor provision system.

25. An atomizer atomiser for a vapor provision system that includes a container for holding a reservoir of free liquid to be vaporized, the atomizer atomiser comprising:
   an atomizing chamber;
   an aperture in a wall of the atomizing chamber to allow a wick to extend from inside the container to inside the atomizing chamber in order to convey the liquid from the reservoir to the inside of the atomizing chamber for vaporization; and
   a resilient seal provided in the aperture to restrict the liquid from entering the atomizing chamber from the reservoir except by travelling along the wick;
   wherein the resilient seal is provided as a lip seal comprising a resilient ridge formed on the inside of the aperture and protruding at least partly into the aperture, wherein the lip seal is at least one of compressed or and/or deflected when the wick is located in the aperture.

26. An atomizer for a vapor provision system that includes a container for holding a reservoir of free liquid to be vaporized, the atomizer comprising:
   an atomizing chamber;
   an aperture in a wall of the atomizing chamber to allow a wick to extend from inside the container to inside the atomizing chamber in order to convey the liquid from the reservoir to the inside of the atomizing chamber for vaporization; and
   a resilient seal provided in the aperture to restrict the liquid from entering the atomizing chamber from the reservoir except by travelling along the wick;
   wherein the atomizing chamber includes first and second opposing side walls, the atomizing chamber being formed between the first and second opposing side walls, and the container for holding free liquid being provided outside the first and second opposing side walls,
   wherein the wick extends through a first aperture in the first side wall and a second aperture in the second side wall,
   and wherein a first resilient seal is provided in the first aperture and a second resilient seal is provided in the second aperture to restrict the liquid from entering the atomizing chamber from the reservoir except by travelling along the wick.

* * * * *